(12) United States Patent
List et al.

(10) Patent No.: US 11,389,586 B2
(45) Date of Patent: Jul. 19, 2022

(54) SUPERVISION DEVICE FOR AMBULATORY INFUSION

(71) Applicant: Roche Diabetes Care, Inc., Indianapolis, IN (US)

(72) Inventors: Hans List, Oberzent (DE); Frederic Wehowski, Hockenheim (DE)

(73) Assignee: ROCHE DIABETES CARE, INC., Indianapolis, IN (US)

( * ) Notice: Subject to any disclaimer, the term of this patent is extended or adjusted under 35 U.S.C. 154(b) by 0 days.

(21) Appl. No.: 16/326,752

(22) PCT Filed: Sep. 4, 2017

(86) PCT No.: PCT/EP2017/072049
§ 371 (c)(1),
(2) Date: Feb. 20, 2019

(87) PCT Pub. No.: WO2018/046420
PCT Pub. Date: Mar. 15, 2018

(65) Prior Publication Data
US 2019/0175828 A1 Jun. 13, 2019

(30) Foreign Application Priority Data
Sep. 6, 2016 (EP) .................................. 16187477

(51) Int. Cl.
*A61M 5/168* (2006.01)
*A61M 5/36* (2006.01)
(Continued)

(52) U.S. Cl.
CPC .......... *A61M 5/1684* (2013.01); *A61M 5/142* (2013.01); *A61M 5/16831* (2013.01);
(Continued)

(58) Field of Classification Search
CPC .... A61M 5/142; A61M 5/172; A61M 5/1684; A61M 5/16831; A61M 2205/3673;
(Continued)

(56) References Cited

U.S. PATENT DOCUMENTS 4,784,643 A 11/1988 Siretchi et al.
6,813,944 B2 11/2004 Mayer et al.
(Continued)

FOREIGN PATENT DOCUMENTS

EP  0 121 848   10/1984
EP  1 177 802   2/2002
(Continued)

OTHER PUBLICATIONS

Stachowiak, H. et al., "A thermoelectric sensor for fluid flow measurement, principles, calibration and solution for self temperature compensation." Flow Measurement and Instrumentation 9 (1998) 135-141. 8 pages.

*Primary Examiner* — Amber R Stiles
*Assistant Examiner* — Avery Smale
(74) *Attorney, Agent, or Firm* — Woodard, Emhardt, Henry, Reeves & Wagner, LLP

(57) ABSTRACT

Disclosed is a supervision device (9) for supervising liquid drug flow in a flow channel (20). The supervision device (9) includes a flow detector (1), arranged for operatively coupling with the flow channel (20) and generating a flow detector signal in dependence of a flow in the flow channel (20) at a flow detection location. The supervision device (9) further includes a gas detector (8), arranged for operatively coupling with the flow channel (20) and generating a gas detector signal in dependence of whether liquid drug or gas is present in the flow channel (20) at a gas detection location at a distance upstream from the flow detection location. The supervision device (9) further includes a processing unit (90)
(Continued)

in operative coupling with the flow detector (1) and the gas detector (8), wherein the processing unit (90) is configured to determine, based on the gas detector signal, whether non-flowing liquid drug is present at the flow detection location or a gas bubble passes the flow detector if the flow detector signal does not indicate a liquid drug flow.

15 Claims, 8 Drawing Sheets

(51) Int. Cl.
 *A61M 5/142* (2006.01)
 *A61M 5/172* (2006.01)
(52) U.S. Cl.
 CPC ............ *A61M 5/172* (2013.01); *A61M 5/365* (2013.01); *A61M 2005/16868* (2013.01); *A61M 2005/16872* (2013.01); *A61M 2205/18* (2013.01); *A61M 2205/3306* (2013.01); *A61M 2205/3317* (2013.01); *A61M 2205/3334* (2013.01); *A61M 2205/3379* (2013.01); *A61M 2205/3673* (2013.01); *A61M 2205/50* (2013.01)
(58) Field of Classification Search
 CPC .......... A61M 2005/16868; A61M 2205/3379; A61M 2205/3334; A61M 2005/16872; A61M 2205/18; A61M 2205/3306; A61M 2205/3317; A61M 2205/50; A61M 2005/16863; A61M 5/16886; A61M 2205/3331

See application file for complete search history.

(56) References Cited

U.S. PATENT DOCUMENTS

| | | | | |
|---|---|---|---|---|
| 2010/0262078 | A1* | 10/2010 | Blomquist | .......... A61M 5/1452 |
| | | | | 604/151 |
| 2013/0237955 | A1* | 9/2013 | Neta | .................. A61M 5/16831 |
| | | | | 604/500 |
| 2015/0246175 | A1* | 9/2015 | Shubinsky | ............ A61M 5/365 |
| | | | | 604/500 |
| 2016/0175519 | A9* | 6/2016 | Lee | .................... A61M 5/16831 |
| | | | | 604/67 |

FOREIGN PATENT DOCUMENTS

| | | |
|---|---|---|
| EP | 1 970 677 A1 | 9/2008 |
| EP | 2 163 273 A1 | 3/2010 |
| EP | 2 361 646 A1 | 8/2011 |
| EP | 2 457 602 A1 | 5/2012 |
| EP | 2 510 960 A1 | 10/2012 |
| EP | 2 510 962 A1 | 10/2012 |
| EP | 2 510 962 A1 | 10/2017 |
| JP | 2012522583 | 9/2012 |
| WO | WO 2009/114115 A1 | 9/2009 |
| WO | WO 2012/059209 A1 | 5/2012 |
| WO | WO 2012/069308 A1 | 5/2012 |
| WO | WO 2012/140063 | 10/2012 |
| WO | WO 2013/029999 A1 | 3/2013 |
| WO | WO 2013/034159 A1 | 3/2013 |

* cited by examiner

SUPERVISION DEVICE FOR AMBULATORY INFUSION

CROSS-REFERENCE TO RELATED APPLICATIONS

This application is the National Stage of International Application No. PCT/EP2017/072049, filed Sep. 4, 2017, which claims the benefit of EP Application No. 16187477.1, filed Sep. 6, 2016, the entire disclosures of which are hereby incorporated by reference.

TECHNICAL FIELD

The present disclosure lies in the field of ambulatory infusion systems and ambulatory infusion devices, as used in a number of therapies, in particular diabetes therapy. More particularly, the disclosure lies in the field of supervising the liquid drug administration.

BACKGROUND AND PRIOR ART

Continuous subcutaneous insulin infusion (CSII) is an established state-of the art therapy of diabetes mellitus. It is carried out via sophisticated computer-controlled ambulatory infusion devices that are commercially available from a number of suppliers. Traditionally, such ambulatory infusion devices are realized as miniaturized syringe driver devices and are worn, e.g., in a trousers' pocket, with a belt clip, or the like. Recently, alternative devices have been developed that are directly attached to the patient's skin. Also alternative fluidic designs have been proposed, e.g. downstream dosing architectures with a variable intermediate dosing cylinder, as disclosed, e.g., in EP1970677A1. In this context, the phrase "downstream dosing" refers to the fact that for such architectures metering is not achieved by controlled displacing a plunger of the primary reservoir with the drive being accordingly arranged upstream of the primary reservoir, but the dosing cylinder out of which the liquid drug is metered is downstream of the primary reservoir. While diabetes therapy is a major field of application of ambulatory infusion devices, they may also be used in further therapies, such as cancer therapy and pain therapy.

While substantive improvements have been made over the years regarding many aspects, supervising the administration is still an issue of concern. In particular, liquid drugs such as insulin may occasionally and under adverse circumstances clog the infusion tubing or infusion cannula, resulting in an occlusion. According to the state of the art, occlusions are detected indirectly, e.g. by measuring and evaluating a reaction force in the drive chain, which significantly and continuously increases in case of an occlusion. However, since the overall system elasticity is low but still present, and because the typical drug administration rates according to a basal delivery schedule may be very low, in particular for children and juveniles, and further in view of large uncertainties that result, e.g., from a variable piston friction in syringe-driver systems, the delay time until an occlusion is detected may be significantly and in the range of many hours and potentially up to a day or more. At the same time, false alarms are cumbersome and should be avoided as far as possible.

SUMMARY OF DISCLOSURE

In view of this situation, it has been proposed to directly measure the liquid drug flow. Thermal flow sensors that may be used for this purpose typically include a heating element and two temperature sensors that are arranged upstream respectively downstream from the heating element, with the heating element and the temperature sensors being thermally coupled to the liquid. For the liquid being in rest (i.e. no flow being present), thermal energy that is emitted from the heating element is thermally conducted by the liquid to both temperature sensors which accordingly measure an identical heat increase (assuming a symmetrical setup). If, however, a liquid flow is present from "upstream" towards "downstream", the thermal energy is largely transported downstream, resulting in the downstream temperature sensor measuring a higher temperature as compared to the upstream temperature sensor, with the temperature difference being indicative for the liquid velocity.

In principle, such thermal flow sensor may be suited for monitoring the operation of an ambulatory infusion system as explained before. It has to be considered, however, that all liquid-contacting elements need to be sterile and further need to be realized as disposables with a limited lifetime of a few days up to, e.g., two weeks. Ideally, the flow sensor would accordingly also be designed as sterile disposable. For a number of reasons related to handling, manufacture and in particular costs, however, such approach is undesirable and largely unfeasible.

When providing the heating element and the temperature sensors as part of the ambulatory infusion device with a releasable coupling to a flow channel, e.g. a piece of tubing, however, a good thermal coupling e.g. with the tubing walls is hard to achieve.

The Wo2012/0592009 discloses a thermal flow sensor of the above-mentioned type, where the heating element and the temperature sensors are arranged as standard surface-mounted components on a spring-loaded suspension that is pressed against a tubing wall with a contact force. Due to the very limited space in ambulatory infusion devices, however, some amount of curvature or bending is typically present in the tubing, resulting in an at least partly insufficient thermal coupling. Small flow rates respectively an administration of small liquid drug amounts is therefore impossible to supervise.

The U.S. Pat. No. 6,813,944 discloses an alternative design where the heating element and the temperature sensors are implemented on a common piece of semiconductor substrate to which the flow channel directly couples. While this approach is advantageous from a thermal point of view, it requires a separation between the (disposable) flow channel and the (durable) flow sensor as part of an infusion device directly at the semiconductor, such that the semiconductor and its tiny bonding wires are freely accessible and unprotected whenever the disposable flow channel is exchanged. Such setup is accordingly unfeasible from a practical and handling point of view.

Furthermore, flow detectors or flow sensors that are sufficiently robust, simple to handle and sufficiently cheap to be used in the present context can, in a situation where no liquid drug flow is detected even though the ambulatory infusion device is administering drug, in particular drug pulses, not distinguish whether there is actually no flow because of an occlusion, or whether a gas bubble that is present in the liquid drug stream is passing the flow sensor or flow detector. The signal that is obtained from the temperature sensors is similar or even identical in both cases.

It is an overall objective of the present disclosure to improve the situation regarding the use or flow detectors, in particular thermal flow detectors for monitoring or supervising the liquid drug administration by an ambulatory infusion system. Favorably, disadvantages of the prior art as discussed before are reduced or avoided.

The objective is achieved by providing a gas detector upstream of the flow detector and evaluating the signal(s) as provided by the flow detector differently in dependence of a gas detector signal that is provided by a gas detector. Further objectives that are achieved by a particular embodiments are described further below in their specific context.

More specifically, the overall objectives are achieved by the subject matter of the independent claims. Favorable and exemplary embodiments being defined by the dependent claims as well as the overall disclosure.

When referring, in the context of the present document, to a liquid drug, such liquid drug may in particular be aqueous liquid drug solution, in particular a liquid insulin formulation. The thermal and optical properties as well as the flow characteristics are water-like. The liquid drug may, however, also be any other pharmaceutical that may be administered via an ambulatory infusion system, such as pain killers or cancer drugs.

When referring, in the context of the present document, to gas, such gas is typically air but may also another gas of air-like characteristics, in particular optical characteristics.

According to an aspect, the overall objective is achieved by a supervision device for supervising liquid drug flow in a flow channel. The supervision device includes a flow detector that is arranged for operatively coupling with the flow channel and generating a flow detector signal in dependence of a flow in the flow channel at a flow detection location. The supervision device further includes a gas detector that is arranged for operatively coupling with the flow channel and generating a gas detector signal in dependence of whether liquid drug or gas is present in the flow channel at a gas detection location at a distance upstream from the flow detection location. The gas detector may in particular be configured to detect a gas bubble passing the gas detector respectively the gas detection location, respectively liquid-to-gas transitions and gas-to-liquid transitions passing gas detection location. The supervision device further includes a processing unit in operative coupling with the flow detector and the gas detector, wherein the processing unit is configured to determine, based on a the gas detector signal, whether non-flowing liquid drug is present at the flow detection location or a gas bubble passes the flow detector if the flow detector signal does not indicate a liquid drug flow.

An area where the flow channel couples, in an operational configuration, with the flow detector, is also referred to as flow detector coupling area. Similarly, an area where the flow channel couples, in an operational configuration, with the gas detector, is also referred to as gas detector coupling area. The flow detector coupling area and the gas detector coupling area are, in combination, also referred to as channel coupling area. The channel coupling area in relation to the gas detector and the flow detector, in particular in relation to the elements that operatively couple to the flow channel, is defined by the design of the supervision device. The phrase "operational configuration" refers to a configuration as present during use where the flow detector and the gas detector are operationally coupled to the flow channel.

Typically, the gas detector further includes a gas detector evaluation unit and the flow detector includes a flow detector evaluation unit. The evaluation units are operatively coupled to sensing elements of the flow detector and the gas detector respectively, e.g. thermoelectric elements or temperature sensors of a thermal flow detector and optical receivers for an optical gas detector. As output, the flow detector evaluation unit provides the flow detector signal and the gas detector evaluation provides the gas detector signal to the processing unit.

In the context of an ambulatory infusion system and the present disclosure, the flow direction of the liquid drug is generally known, resulting in "upstream" and "downstream" being well defined. For a reversed flow direction, however, the role of "upstream" and "downstream" elements is simply reversed. In a general sense, "upstream" and "downstream" may, when referring to particular elements or components, be read as "first" and "second", resulting in a wording independent from the flow direction.

In operation, a volumetric metering pump is arranged upstream of the supervision device and the supervision device is configured for use in combination with a volumetric metering pump. A volumetric metering pump is configured to deliver well-defined liquid volumes largely independent of other influence factors, in particular pressure. Volumetric metering pumps that are used in the context of ambulatory infusion pumps are typically piston pumps where the delivered liquid volume is controlled via a piston displacement, normally using a spindle drive. This basic design is given for both ordinary syringe drivers as well as for downstream dosing systems with a dosing unit as explained before. The volumetric metering pump is configured to administer drug pulses of fixed and/or variable drug pulse volume with a fixed and/or variable time interval. A drug pulse is administered within a short (and often negligible) time period and no or only negligible drug flow is present in the flow channel between the pulses.

In an embodiment, the flow detector is a thermal flow detector and the gas detector is an optical gas detector as discussed further below in more detail. In alternative embodiments, however, either or both of the flow detector and the gas detector may be designed differently and operate according to other principles that are generally known in the art. In an embodiment with an optical gas detector, the flow channel is, at least in the gas detector coupling area, transparent for radiation that is emitted by an emitter of the gas detector, e.g. in the visible and/or infrared (IR) range.

In a typical embodiment, the gas detector and the flow detector are not operated continuously, but only during drug administration, in particular for the administration of drug pulses in the context of basal drug delivery. Where not explicitly mentioned, the flow detector signal not indicating liquid drug flow generally refers to a point in time where the drive unit of an ambulatory infusion device is controlled to administer a liquid drug, in particular a liquid drug pulse, and a liquid flow or change of liquid flow is accordingly expected.

Further, the flow channel is, at least in the flow detector coupling area and/or the gas detector coupling area, favorably flat and has substantially flat and parallel opposing channel walls for good coupling of the (optical) gas detector and (thermal) flow detector, respectively.

The gas detector signal is generally a binary signal that depends on whether liquid drug or gas is present in the flow channel at the gas detection location. The flow detector signal may be a continuous signal that is indicative of the flow speed (of liquid drug) and/or the change of flow speed in the flow channel at the flow detection location. In the following, however, the flow detector signal is assumed as binary signal that depends on whether or not a flow and/or a change of flow is present. While liquid drug is largely incompressible, the volume of a gas bubble and accordingly the length of a gas bubble inside the flow channel varies with the pressure. Here, it is assumed that the pressure is substantially constant for the relevant time period of a gas bubble passing the gas detector, the flow detector, and the section of the flow channel between them, resulting in the length of the gas bubble being substantially constant for a constant cross section of the flow channel.

The flow detection location is determined by the flow detector coupling area. Similarly, the gas detection location is determined by the gas detector coupling area. "Upstream" and "down-stream" are to be understood with respect to the flow direction inside the flow channel.

In the context of the present disclosure, it is assumed that the flow detection location and the gas detection location extend along the flow channel by a distance that is sufficiently small to be considered as spot or point.

The flow channel may be straight or curved in the flow detector coupling area and/or the gas detector coupling area. While various arrangements are possible, a straight flow channel is favorable at least in the flow detector coupling area for typical flow detector designs, in particular thermal flow detectors. A straight flow channel is exemplarily assumed in the following.

The flow channel has a constant cross section within the flow detector coupling area. This is given as well within the gas detector coupling area and typically also within the distance between the both. These three cross sections may differ from each other but are design-given and therefore known. During a drug administration (also referred to as flow event), the displaced volume in each section of the channel (more generally: the volume that passes each of the section per time) is identical, while the flow speed and the displacement of an infinitesimal liquid volume element in the flow direction may differ in dependence of the cross sectional area. The constant volume can be computed as the product of the actual (constant) cross sectional area and an actual distance along the respective section of the flow channel. As a consequence, the distance along the flow direction, by which a gas bubble, and in particular the downstream front and the upstream front of a gas bubble is displaced for a given displaced volume, is generally different for the gas detector coupling area, the flow detector coupling area, and the section of the flow channel inbetween them.

All cross sections are small enough to separate liquid from gas by surface tension. As result, no mixture of gas and liquid is present. In case a mixture of gas and liquid is fed into the channel, there will be a sequence of liquid and gas portions. Once primed, the liquid system mainly is filled with liquid and occasionally gas bubbles may occur.

In the context of the present document, the "flow channel" means a duct with a lumen that is, during operation, filled with liquid drug, potentially including gas bubbles, over its total cross sectional area and is further surrounded by a wall or an arrangement of walls along its whole circumference. The coupling of the flow channel with the supervision device is accordingly a thermal and mechanical coupling with an outer wall surface of the flow channel. The flow channel may be a length of tubing of usually circular cross section. Other designs of the flow channel, however, are possible as well. The flow channel may in particular be realized by a groove or depression in a substantially rigid and e.g. injection-moulded component. At its open side, the groove or channel is covered by foil. The thickness of such foil may be in a typical range of 20 Micrometres to 200 Micrometres. For such design, the thermoelectric elements contact, in an operational configuration, the foil of the flow channel. This type of design is particularly suited in the context of thermal flow detection or flow measurement because the thermal transfer resistance is typically considerably lower as compared to tubing.

The flow channel is typically part of a one-way fluidic device that is coupled to an ambulatory infusion device for a limited application time of typically a number of days up to, e.g., two weeks, via corresponding mating couplers as discussed further below in more detail. Therefore, the phrase "releasable" coupling refers, in the context of the present document, to a coupling that is, after being established e.g. by a user, self-maintaining and may be released without damaging the supervision device or other parts of an ambulatory infusion device of which the supervision device may be part of. Furthermore, the releasable coupling allows a sequential coupling of the supervision device with a number of flow channels respectively of an ambulatory infusion device with a number of fluidic one-way components in sequence. The arrangement is such that the gas detector couples to the flow channel in the gas detector coupling area and the flow detector couples with the flow channel in the flow detector coupling area. A fluidic component that includes the flow channel may also be realized as dosing unit according as disclosed, e.g., in EP1970677A1, EP1970677A1, EP2510962, EP2510960, EP2696915, EP2457602, WO2012/069308, WO2013/029999, EP2753380, EP2163273, and EP2361646.

The supervision device may include a flow channel positioning structure. A flow channel positioning structure is designed to position the flow channel relative to the flow detector and the gas detector, thereby defining the flow detector coupling area with the flow detection location, and the gas detector coupling area with the gas detection location.

The positioning structure may be designed to directly contact and guide the flow channel such that coupling with the gas detector and the flow detector is given. In such embodiment, the positioning structure may, e.g., be realized by a grove-carrying element, wherein the groove is designed to receive the flow channel e.g. in form of a length of tubing.

In an embedment where the flow channel is part of a fluidic device with a well-defined geometric arrangement, the positioning structure may be or include a mating coupler, in particular a fluidic device coupler, that is designed to mate with a corresponding counter mating coupler, in particular an infusion device coupler of the fluidic device, such that the flow channel is correctly positioned. Optionally, the positioning structure may also serve as abutment that absorbs the biasing forces that are exerted by first biasing element, second biasing element and optional third biasing element. As discussed further below in more detail, the fluidic device coupler may be part of an ambulatory infusion device that comprises the supervision unit.

The flow detector and the gas detector are typically in fixed geometric arrangement with respect to each other and may be coupled to and/or mounted on a support structure.

A flow detector in accordance with the here as well as further below-described types may be designed and operated to quantitatively measure a flow rate or flow velocity of liquid drug within the flow channel. As will be discussed in more detail further below, however, it is typically operated in a binary way to indicate whether or not a flow of liquid (above a threshold and/or within a given range) occurs at a specific point in time or within a specific time window. Therefore, the flow detector may, in some embodiments, not be sufficiently accurate for a quantitative measurement.

The flow detector signal that is generated by the flow detector if no flow and/or change of flow is detected is also referred to as "no-flow signal". The flow detector is designed to detect a flow and/or change of flow of liquid drug. In case of gas being present at the flow detection location instead of liquid, the signal that is generated by the flow detector may be a no-flow signal, independent on whether the gas is moving. Via the gas detector being arranged upstream of the flow detector, these situations can be distinguished by a supervision device in accordance with the present disclosure.

In an embodiment, the supervision device is configured to determine that the flow detector signal not indicating a liquid drug flow is indicative for a gas bubble passing the flow detector if it occurs an expected delay volume after the gas detector detecting the passing of the gas bubble. The expected delay volume corresponds to the inner volume of the flow channel between the gas detection location and the flow detection location. The expected delay volume is the volume that is expected to be administered between the gas bubble passing the gas detection location and the flow detection location. As discussed further below in more detail, both the downstream front and the upstream front of a gas bubble, having passed the gas detection location, are expected to pass the flow detection location after the administration of the expected delay volume. Because the liquid flow is from upstream to downstream, both the gas detection location and the flow detection location are passed by the downstream front of a gas bubble and subsequently by its upstream front.

In another embodiment, an expected delay time for the occurrence of a no-flow signal may be computed as follows: Once the gas detector detects a liquid-to-gas transition as downstream front of a gas bubble, the subsequently administered volume is summed up respectively integrated as a function of time until the summed up respectively integrated volume corresponds to the inner volume of the flow channel between the gas detection location and the flow detection location (i.e. the expected delay volume as explained before). The summing-up time respectively integration time corresponds to the expected time of the downstream front of the gas bubble passing the flow detection location.

Since the expected delay volume is the volume that is displaced respectively administered in the expected delay time, the expected delay time and the expected delay volume may be converted into each other.

Similarly, once the gas detector detects a gas-to-liquid transition as upstream front of a gas bubble, the subsequently administered volume may be summed up respectively integrated as a function of time until the summed up respectively integrated volume corresponds to the inner volume of the flow channel between the gas detection location and the flow detection location. The summing-up time respectively integration time corresponds to the expected time of the upstream front of the gas bubble passing the flow detection location. Upon the upstream front of the gas bubble passing the flow detection location, the flow detector signal is expected to change from the no-flow signal to a signal indicating a liquid flow.

For the case of a drug administration according to a known (typically pre-programmed) basal administration schedule, the expected delay times may be directly computed upon the liquid-to-gas transition respectively gas-to-liquid transition passing the gas detection location. If, however the administration schedule is modified e.g. by a user command and/or automatically based on a sensor signal, for example a continuous glucose sensor signal, or if drug boluses are administered on demand, the summing up respectively integration as explained before must be carried out continuously. This is a typical case for example in CSII.

In an embodiment, the supervision device is configured to generate an alarm signal if non-flowing liquid drug is present at the flow detection location.

A situation of no drug flow (no-flow signal) even though drug should be administered is generally indicative for an occlusion respectively blockage of the flow channel, respectively the infusion tubing and/or infusion cannula, and should accordingly trigger the generation of a corresponding alarm signal. The same holds true in a situation of no drug flow due to a device error.

In an embodiment, the supervision device may optionally further be configured to command an ambulatory infusion device as discussed further below to stop drug administration in this case.

If a no-flow signal, in contrast, results from the passage of a gas bubble, generating an alarm is generally not required and operation can continue. In an embodiment, however, the supervision device is configured to determine the bubble volume and to generate an alarm if the bubble volume exceeds a predetermined volume.

A number of liquid drugs, in particular liquid insulin formulations, are typically administered into the subcutaneous tissue. In contrast to the infusion into a vein, the infusion of smaller gas/air volumes is less critical in this case. The infusion of larger gas/air volumes, however, should be avoided for principal reasons. Also, if gas/air is administered instead of drug over a prolonged time period of, e.g. a number of hours, the resulting lack in administered drug may be therapeutically significant and cause adverse medical complications (e.g. hyperglycemia in case of insulin). Furthermore, larger bubbles may be indicative for a leakage or generally a hazardous situation.

In an embodiment, the supervision device is configured to determine a gas bubble volume based on the gas detector signal, and to determine subsequently whether the flow detector signal matches the gas bubble volume. The gas bubble volume that is determined via the gas detector by evaluating the gas detector signal is the volume that is displaced respectively administered between the liquid-to-gas transition (downstream front) and the following gas-to-liquid transition (upstream front) passing the gas detection location. After displacing an expected delay volume as explained before, the same gas volume is expected to pass the flow detection location. Therefore, the flow detector signal can be expected to change to the no-flow signal after administering the expected delay volume following the downstream front of a gas bubble passing the gas detection location. Subsequently, the now-flow signal can be expected to be present while displacing respectively administering a volume that corresponds to the bubble volume as determined with the gas detector. A major mismatch (beyond measurement uncertainty) is indicated for a technical defect or generally a hazardous situation.

To put it differently, the gas bubble volume of one and the same gas bubble may be determined independently via the gas detector and subsequently via the flow detector (since the displaced volume is the same at the gas detection location and the flow detection location), and it may be determined whether the two determined volumes match respectively correspond to each other.

A suited gas detector that may be used in the supervision device is based on the fact that an incident (optical) beam that is emitted by optical emitter and hits the outside of the (transparent) flow channel wall in a suited (non-perpendicular) angle passes through and exits the flow channel at an opposite side if liquid is present inside the flow channel. The position where the incident beam that hits the flow channel is the gas detection position. If however, gas is present rather than liquid in the flow channel at the gas detection location, the incident light beam does not mainly pass through the flow channel but increased reflection occurs at the inner surface of the flow channel wall due to the large step in refractive index and most of the light does not pass. This relation holds true if the refractive index of the liquid and of the flow channel wall material is sufficiently close to each other (in particular considerably larger than 1) and different from, in particular larger than, the refractive index of a gas that forms gas bubbles (typically air as mentioned before, having a refractive index of 1).

In an embodiment, an optical emitter (typically an LED or IR LED) and an optical detector (typically a photo transistor) may accordingly be arranged such that a reflected optical beam hits the optical detector but an optical beam passing through the flow channel does not hit the optical detector. In a reversed arrangement, reflected optical beam does not hit the optical detector but a passing optical beam hits the detector.

In an embodiment, the gas detector includes a first optical emitter, a second optical emitter, and an optical detector. The first optical emitter is designed to emit the first optical beam and the second optical emitter is designed to emit a second optical beam. As explained before, a single optical emitter and the single optical detector are in principle sufficient to determine whether gas or liquid is present at the gas detection location. An arrangement with two optical emitters, however, is favorable with respect to reliability and safety, especially it is more independent from ambient light.

In an embodiment with a first optical emitter, a second optical emitter and an optical detector, the first optical emitter and the second optical emitter may be arranged such that the flow channel extends between them. With other words, the first optical emitter and the second optical emitter are arranged on opposite sides of the flow channel. The first optical emitter, the second optical emitter, and the optical detector for this type of embodiment are arranged and oriented with respect to each other such that a first optical beam originating from the first optical emitter hits the optical detector in case of high reflection of the first optical beam, while a second optical beam originating from the second optical emitter hits the optical detector if passing through the flow channel.

In an embodiment with the first optical emitter, a second optical emitter and an optical detector, the first optical emitter, the second optical emitter and the optical detector may be arranged such that a first optical beam that is emitted by the first optical emitter passes through the flow channel without hitting the optical detector and that a second optical beam that is emitted by the second optical emitter passes through the flow channel and hits the optical detector if liquid drug is present inside the flow channel at the gas detection location. In contrast, the first optical beam is reflected and hits the optical detector and that the second optical beam is reflected without hitting the optical detector if gas is present inside the flow channel at the gas detection location.

Via such arrangement it is ensured that the optical beam originating from one of the first optical emitter and the second optical emitter hits the optical detector, while the optical beam originating from the other optical emitter does not hit the optical detector, in dependence on whether liquid or gas is present in the flow channel at the gas detection location. In this way, both the presence of liquid and gas may be positively detected. For a flow detector with a single optical emitter and a single optical detector, a situation where the optical beam does not hit the detector cannot be distinguished from a situation where the gas detector does not operate as intended e.g. due to a defect or the presence of dirt in the optical path. In an embodiment with the first optical emitter and the second optical emitter, the supervision device is configured to control the first optical emitter to vary the first optical beam and to control the second optical emitter to vary the second optical beam with a defined timing relation. The processing unit is configured to determine, based on the timing relation, whether an optical beam that hits the optical detector is the first optical beam or the second optical beam. The expression "varying the optical beam" means a variation or modulation of the light intensity.

In an embodiment, the first optical emitter and the second optical emitter may be activated or switched on and emit an optical beam only alternatively. The processing unit for this type of embodiment determines that an optical beam that hits the optical detector originates from the first optical emitter if the first optical emitter is active (switched on) and the second optical emitter is switched off (inactive). Likewise, an optical beam that hits the optical detector originates from the second optical emitter if the first optical emitter is switched off (inactive) and the second optical emitter is switched on (active).

In a further embodiment, both optical emitters are controlled to emit light simultaneously, but with an (e.g. sinusoidal) time-varying intensity and defined phase relation between the first optical beam and the second optical beam. For this type of embodiment, the processing unit is phase sensitive and comprises, for example, a lock-in circuit. The processing unit determines whether the intensity of the optical beam that is received by the optical detector is in his with the control signal of the first optical emitter or the second optical emitter.

In an alternative, both optical emitters are configured to emit light of different wavelength and the optical detector is configured to determine the wavelength of the incident light.

In a further alternative, only one of the optical emitters, in particular the optical emitter for which the optical beam hits the optical detector in case of liquid at the gas detection location, is activated during regular operation. Under regular operation conditions, the optical detector should accordingly be hit by an optical beam whenever the optical emitter is switched on (activated). Only if the optical detector is not hit by the optical beam, the other optical emitter is switched on (activated) in order to distinguish between the presence of gas at the gas detection position and an error or hazardous situation as explained before.

It is noted that the gas detector of the before-described type may also be favorably used in other applications and without a flow detector. The right for seeking protection for such subject matter is explicitly reserved.

It is noted, however, that this supervision device in accordance with the present disclosure may also use another type of gas detector. For example, a gas detector of generally similar design as described before may be realized with one optical emitter and two optical receivers that are arranged such that one of the optical receivers is hit by the majority of light in dependence of whether liquid drug or gas is present at the gas detection location while the other optical detector receives substantially less light. Further, a gas detector with only a single optical emitter and a single optical detector may be used. Further, a non-optical gas detector as generally known in the art, for example a galvanic gas detector that is based on different conductivities of liquid drug and gas, or capacitive gas detector that is based on different dielectric properties of liquid drug and gas, may be used. In any case, the gas detector is designed to differentiate between liquid and gas, respectively to determine whether liquid or gas is present in the flow channel at the gas detection location.

In an embodiment, the flow detector includes an upstream thermoelectric element and a down-stream thermoelectric element. The upstream thermoelectric element and the downstream thermoelectric element are arranged spaced apart from each other and movable independent from each other. The flow detector may further include an upstream biasing element and a down-stream biasing element. The upstream biasing element acts on the upstream thermoelectric element, thereby biasing the upstream thermoelectric element towards a channel coupling area. The downstream biasing element acts on the downstream thermoelectric element, thereby biasing the downstream thermoelectric element towards the channel coupling area independently from the upstream biasing element. In an embodiment, the upstream thermoelectric element and the downstream thermoelectric element are surface-mounted components. As mentioned before, the part of the channel coupling area where the flow detector couples with the flow channel in an operational configuration is the flow detector coupling area.

The upstream thermoelectric element and the downstream thermoelectric element are in particular arranged spaced apart from each other along an extension direction of the flow channel in an operational configuration. The extension direction of the flow channel corresponds to the axis of the liquid drug flow direction. The first and second thermoelectric elements are in particular movable in a direction traverse to the extension direction of the flow channel, i.e. towards and away from the flow channel in an operational configuration, and may be movable only traverse to the extension direction of the flow channel. The corresponding movements of the thermoelectric elements may be pivoting, bending, or flexing movements, but also, e.g. linear displacement movements.

In an operational configuration, the upstream thermoelectric element couples to the flow channel at an upstream position and the downstream thermoelectric element couples to the flow channel in a downstream position. The flow detector coupling area and in particular the upstream position and the downstream position define the flow detection location.

The downstream thermoelectric element being biased towards the flow channel independently from the upstream thermoelectric element also means that the first biasing element and the second biasing element are functionally independent from each other. The upstream biasing element accordingly exerts an upstream biasing force onto the upstream thermoelectric element and the downstream biasing element independently exerts a downstream biasing force onto the downstream thermoelectric element.

The biasing forces are the contact forces by which the thermoelectric elements are pressed against a wall of the flow channel and are generally oriented traverse to the flow channel, thereby ensuring the required thermal coupling between the flow channel and the thermoelectric elements. For the desirable good thermal coupling, the contact forces should be high. Since the cross sectional area of the flow channel, however, is typically small, the contact forces need to be sufficiently low not to significantly deform the flow channel. Such deformation of the flow channel, resulting in a reduction of the cross section, are likely to cause occlusions and further cause shear forces that result in a number of drugs, such as insulin, to degrade.

For this type of flow detector, the individual biasing of the thermoelectric elements towards the flow channel reduces the tolerance requirements and is in particular suited in designs where some degree of curvature is present in the flow channel in the area of the flow detector. Such situation is typical in fact hardly avoidable for an ambulatory infusion device that is carried substantially continuously night and day and for which small dimensions, i.e. a slim design and a small footprint, are of major importance. It is noted, however, that a supervision device in accordance with the present disclosure is not limited to this particular flow sensor design but other designs may be used as well where appropriate.

Generally, it is desirable to position the thermoelectric elements of a thermal flow detector or flow sensor spaced apart from each other, but as close to each other as possible along the flow channel. Arranging the thermoelectric elements to be separately movable and providing separate biasing elements, however, requires additional space and may therefore be considered as little advantageous. It is found, however, that this disadvantage is more than outbalanced by the improved thermal coupling that may be achieved.

In an embodiment, the flow detector further includes a middle thermoelectric element. The middle thermoelectric element is arranged between and spaced apart from the upstream thermoelectric element and the downstream thermoelectric element. The middle thermoelectric element is movable independent from the upstream thermoelectric element and the downstream thermoelectric element. A flow detector according to this type of embodiment may further comprise a middle biasing element. The middle biasing element acts on the middle thermoelectric element, thereby biasing the middle thermoelectric element towards the channel coupling area independent from the upstream biasing element and the downstream biasing element. In an operational configuration, the middle thermoelectric element couples to the flow channel in a middle position.

Such embodiment with a middle thermoelectric element corresponds, regarding the thermoelectric elements, to a classic design for a thermal flow detector or flow sensor. Here, the middle thermoelectric element is generally a heating element, typically in form of an electric resistor, while the upstream respectively downstream thermoelectric element is an upstream respectively downstream temperature sensor. The arrangement is favorably symmetric, with the upstream thermoelectric element and the downstream thermoelectric element being of identical design and arranged equally spaced apart from the middle thermoelectric element.

For this type of embodiment, the arrangement of the middle thermoelectric element is generally the same as it is the case for the upstream thermoelectric element and the downstream thermoelectric element. Embodiments and characteristics that are in the following discussed in more detail for the upstream and downstream thermoelectric element, such as the way of arrangement on a carrier and the way of coupling to the flow channel, also hold true for the middle thermoelectric element in an analogue way.

In an alternative embodiment, the downstream thermoelectric element operates as downstream temperature sensor and senses a downstream temperature at the downstream position. The upstream thermoelectric element may be configured to operate as heating element, thereby heating liquid inside the flow channel at the upstream position, and to operate as upstream temperature sensor and sense an upstream temperature at the upstream position. This type of embodiment is discussed further below in more detail in the context of another aspect of the present disclosure. This type of embodiment is favorable in so far as only two thermoelectric elements are required, thereby reducing the costs and the installation space of the flow detector.

In an embodiment, the upstream thermoelectric element is carried by an upstream element carrier and the downstream thermoelectric element is arranged on a downstream element carrier, and a gap is present between the upstream element carrier and the downstream element carrier.

Providing the upstream thermoelectric element and the downstream thermoelectric element on different carriers with a gap in between is counter-intuitive in so far as the gap adds to the distance between the thermoelectric elements along the flow channel, which is generally unfavorable. A common carrier, e.g. a common printed circuit board, however, forms a thermal bridge between the thermoelectric elements, resulting in a considerable portion of the heat transfer between the thermoelectric elements occurring via the carrier, rather than the flow channel respectively the liquid within the flow channel, as desired. A gap between the thermoelectric elements, in contrast, increases the thermal insulation because of the low thermal conductivity of the (air) gap, thus enhancing the thermal coupling between thermoelectric elements and flow channel. This favorable effect is found to outweigh the generally negative influence of the increased distance.

In an embodiment with a middle thermoelectric element, the middle thermoelectric element may be arranged on a middle element carrier, and an upstream gap may be present between the upstream element carrier and the middle element carrier along the extension direction of the flow channel, and a downstream gap may be present between the middle element carrier and the downstream element carrier along the extension direction of the flow channel. The setup may be symmetric, with the gaps having the same width.

In an embodiment, the upstream thermoelectric element is arranged on an upstream flexible printed circuit board element and the downstream thermoelectric element is mounted on a downstream flexible printed circuit board element.

In an embodiment with a middle thermoelectric element, the middle thermoelectric element may be arranged on a middle flexible circuit board element in an analogue way.

In such embodiment, the upstream respectively downstream printed circuit board element serve, in addition to carrying the thermoelectric elements, as movable elements for the movable arrangement of the thermoelectric elements. The flexible printed circuit board elements may have an elongated "finger-shaped" design and extend traverse to the flow channel, thereby allowing flexing traverse to the flow channel, resulting in a movement of the thermoelectric elements towards respectively away from the flow channel, traverse to the flow direction respectively extension of the flow channel. For such an arrangement, the flexible printed circuit board elements generally has a flexing area which enable pivoting movement of the thermoelectric elements towards and away from the flow channel respectively the flow detector coupling area.

Typically for such embodiments, the flexible printed circuit board elements extend parallel to each other and maintain their parallel arrangement when flexing. Alternatively, however, the flexible printed circuit board elements may be angled relative to each other. The flexible circuit board elements may be separate from each other and separately attached to a support structure, e.g. a rigid printed circuit board. In a particular embodiment, however, the flexible printed circuit board elements extend from a common flexible printed circuit board base that may be formed integrally with the flexible circuit board elements.

In an embodiment, the upstream thermoelectric element is arranged on an upstream flexible printed circuit board element and the downstream thermoelectric element is arranged on a downstream flexible printed circuit board element, wherein the upstream thermoelectric element is arranged on a side of the upstream flexible circuit board element pointing away from the channel coupling area, in particular the flow detector coupling area, and the downstream thermoelectric element is arranged on a side of the downstream flexible circuit board element pointing away from the channel coupling area. Thermoelectric elements pointing towards respectively away from the channel coupling area implies that, in an operational configuration, they point towards respectively away from the flow channel, when viewed from the corresponding carrier, e.g. flexible printed circuit board element.

In alternative embodiments, the upstream thermoelectric element, the downstream thermoelectric element and an optional middle thermoelectric element may each be arranged on a side of the corresponding printed circuit board element pointing towards the flow channel. For this this type of embodiment, the thermoelectric elements couple directly to the flow channel respectively a wall of the flow channel. In this regard, such arrangement corresponds to a classic thermal flow sensor design. Here the heat exchange between the thermoelectric elements and the flow channel occurs via the housing of the thermoelectric elements.

For an embodiment where the thermoelectric elements are arranged on the sides of the flexible printed circuit board elements pointing away from the flow channel, the flexible printed circuit board elements are, in an operational configuration, situated between the thermoelectric elements and the flow channel, such that the upstream respectively downstream thermoelectric element couples with the flow channel thermoelectric elements couple to the flow channel indirectly via the corresponding flexible printed circuit board, rather than directly. Such arrangement is counter-intuitive in that the indirect coupling in principle downgrades the thermal coupling. However, the primary direction of thermal energy flow from respectively towards the thermoelectric elements is given by the direction of lowest thermal resistance. In dependence of the specific design, the lowest thermal resistance is typically present between the electric contacts respectively contact pads of the thermoelectric elements and the corresponding (typically copper) conductor paths on the flexible printed circuit board elements. This particularly holds true for surface-mounted devices (SMDs) respectively surface-mounted elements. A majority of thermal energy transfer is accordingly via the conductor paths. For an arrangement of the proposed type with the thermoelectric elements being arranged on the sides of the flexible printed circuit board elements pointing away from the flow channel, the flexible printed circuit board elements contact the flow channel and the conductor paths are available for the thermal energy transfer. Thereby, improved thermal coupling may be achieved event if the thermal energy exchange is via the backing material of the flexible printed circuit board elements with comparatively high thermal resistance.

In an embodiment, the upstream thermoelectric element and the downstream thermoelectric element are NTC thermistors of different electric resistance. This arrangement results in an asymmetric electrical design which may be generally used but is particularly favorable in combination with a specially designed evaluation unit as explained below. Alternatively, however, the upstream thermoelectric element and the downstream thermoelectric element may have identical characteristics and may be, e.g., NTCs of identical nominal electric resistance and temperature coefficient. Further alternatively, however, other types of thermoelectric elements may be used, e.g. PN junction semiconductors.

In an embodiment, the flow detector evaluation unit is designed to provide an output signal of variable frequency. The frequency depends on a difference between the upstream temperature as sensed by the upstream thermoelectric element and the downstream temperature as sensed by the downstream thermoelectric element. Such evaluation unit may be implemented in a particularly compact way with a small number of components, based on, e.g., a typical microcontroller according to the state of the art. This type of embodiment may especially be realized based on a Schmitt-Trigger, an oscillator, e.g. an RC oscillator, and a reference voltage supply, wherein the upper and lower threshold of the Schmitt-trigger are determined by the resistance of the upstream thermoelectric element and the downstream thermoelectric element, respectively.

According to a further aspect, the overall objective is achieved by an ambulatory infusion device. The ambulatory infusion device includes a fluidic device coupler, the fluidic device coupler being designed for releasable mating coupling, in an operational configuration, with an infusion device coupler of a fluidic device with a flow channel. The ambulatory infusion device further includes a pump drive unit. The pump drive unit is configured to administer liquid drug out of a drug container to a patient's body via the flow channel. The ambulatory infusion device further includes a pump control unit, configured to control operation of the pump drive unit for continuous drug administration according to a time-variable basal infusion administration rate. The ambulatory infusion device further includes a supervision device according to any embodiment as discussed before and/or further below. The supervision device is in operative coupling with the pump control unit. The supervision device is realized in accordance with the disclosure of the present document. In an operational state, the ambulatory infusion device, the fluidic device and a drug container form a common compact unit.

The pump drive unit and the pump control unit favorably form, in combination with a drug container and/or the fluidic device, a volumetric metering pump that is designed for the administration of liquid drug, in particular insulin, in well-defined doses.

In some embodiments, the pump drive unit includes a spindle drive that is designed to couple with a piston of a—typically, but not necessarily cylindrical—drug cartridge as drug container, such that the piston is displaced inside the drug cartridge in well-defined incremental steps in a syringe-like way. Here, the pump drive unit typically includes a rotatory motor as actuator, a reduction gear, a drive nut and a threaded lead screw in operative engagement with the drive nut, the lead screw being designed for coupling with the piston. Alternatively, the pump drive unit may include the drive nut but not the lead screw which may be permanently coupled to the piston. Instead of a simple lead screw, more advanced arrangements, such as a telescopic drive rod may be used. Syringe-driver pumps are well known for ambulatory infusion devices in a variety of design variants and typically used in state-of-the art systems.

Alternatively, the pump drive unit may be designed to operatively couple to and cooperate with another type of pump unit, such as micro membrane pump or a downstream-dosing unit as disclosed, e.g. in EP1970677A1, EP1970677A1, EP2510962, EP2510960, EP2696915, EP2457602, WO2012/069308, WO2013/029999, EP2753380, EP2163273, and EP2361646. Syringe-driver pumps and downstream-dosing units as mentioned before are examples of positive-displacement metering pumps with a well-defined and design-given relation between pump actuator or pump drive movement and drug administration.

The pump drive unit is favorably designed for the administration of single doses in a range of 1 microliter or below, for example 500 nanoliters, 200 nanoliters, or 100 nanoliters. For the typical concentration U100 for liquid insulin formulations, 1 milliliter of liquid contain 100 International Units (IUs) of insulin.

The ambulatory infusion pump is favorably designed for the metered administration independent form an output signal that is provided by the supervision device, in particular the flow detector, with the supervision device serving for administration monitoring and supervision purposes. This condition is fulfilled for positive-displacement respectively volumetric metering pumps, such as syringe-driver pumps or pumps with a down-stream dosing unit as mentioned before.

In an embodiment of an ambulatory infusion device, the pump control unit is configured to control the pump drive unit to administer drug pulses of pre-set pulse volume and to vary a time between consecutive pulses in dependence of a required basal administration rate, wherein the flow detector is configured to be intermittently operated for the administration of the drug pulses. Alternatively or additionally, the pump control unit may be configured for the administration of drug pulses of variable pulse volume with a constant or variable time between consecutive drug pulses. The control unit may further be configured to control additional the administration of drug boluses of adjustable bolus volume on demand. The administration of a drug pulse is also referred to as "flow event".

In an embodiment, the ambulatory infusion device is configured to determine when a gas bubble reaches the infusion site and to control the pump drive unit to administer a compensation volume, the compensation volume corresponding to the volume of the gas bubble, upon the gas bubble reaching the infusion site.

According to a still further aspect, the overall objective is achieved by an ambulatory infusion system, the ambulatory infusion system including ambulatory infusion device and a fluidic device as discussed above and/or further below.

According to a still further aspect, the overall objective is achieved by a medical assembly, the medical assembly including a supervision device and a fluidic device or a flow channel as discussed above and/or further below.

An ambulatory infusion device and an ambulatory infusion system in accordance with the present disclosure may be designed to be carried by a user and to operate for an extended time period of a number of days up to a number of weeks continuously and concealed from view, e.g. in a trousers pocket, with a belt clip or the like. Alternatively, the ambulatory infusion device or ambulatory infusion system may be designed to be directly attached to a user's skin, e.g. via an adhesive pad, for the extended time period. An ambulatory infusion device and an ambulatory infusion system in accordance with the present disclosure are designed to operate and administer liquid drug independent from an orientation with respect to gravity.

According to a further aspect, the overall objective is achieved by a method for supervising liquid drug administration via a flow channel. The method includes generating a flow detector signal in dependence of a flow in the flow channel at a flow detection location. The method further includes generating a gas detector signal in dependence of whether liquid drug or gas is present in the flow channel at a gas detection location at a distance upstream from the flow detection location. The method further includes determining, based on the gas detector signal, whether a the flow detector signal not indicating a liquid drug flow is indicative of situation of no drug flow or of a gas bubble at the flow detection location.

In an embodiment, the method includes generating an alarm signal if the flow detector signal not indicating a liquid drug flow signal is indicative of a situation of no drug flow.

Methods in accordance with the present disclosure may be carried out by devices, in particular supervision devices and/or ambulatory infusion devices, in accordance with the present disclosure.

Specific embodiments of disclosed devices, in particular supervision devices and/or ambulatory infusion devices disclose, at the same time corresponding method embodiments. In the same way, specific embodiments of disclosed methods disclose, at the same time, corresponding devices, in particular supervision devices and ambulatory infusion devices.

WAYS OF CARRYING OUT THE INVENTION

Figure 1:
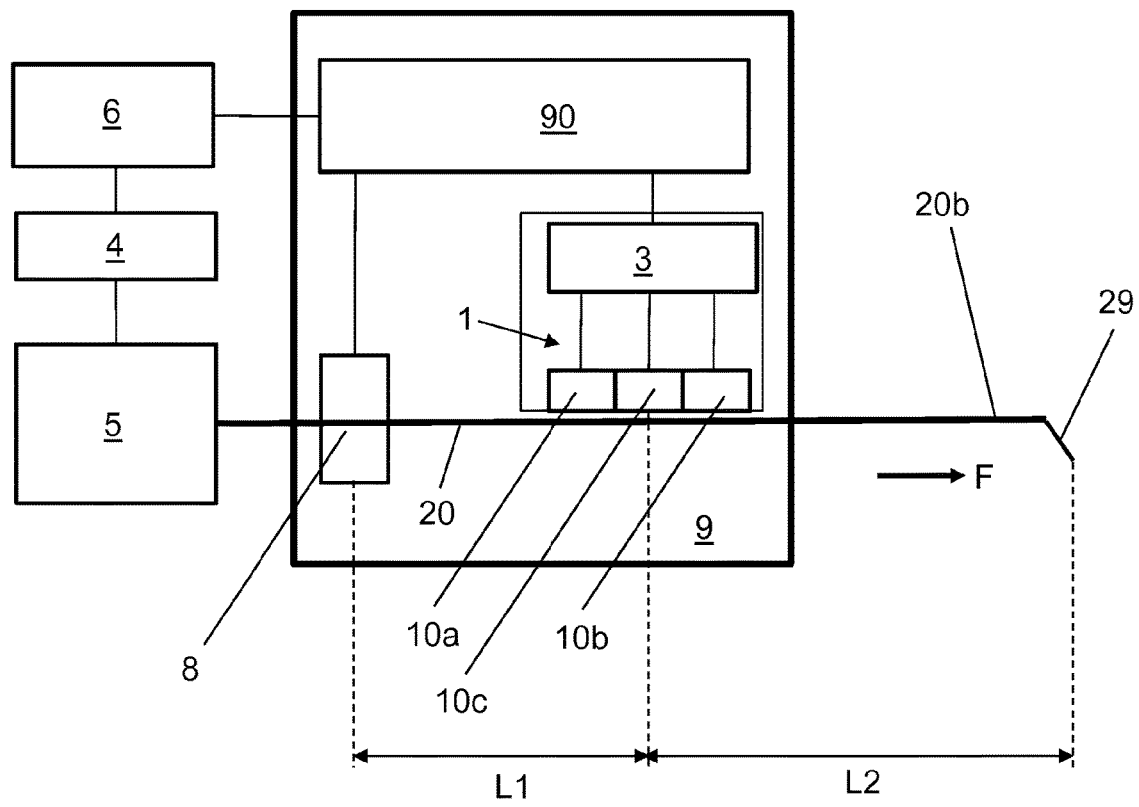
FIG. 1 schematically shows an embodiment of a supervision device in operative coupling with further related elements.

In the following, reference is first made to FIG. 1, showing an exemplary embodiment of a supervision device 9 in accordance with the present disclosure in a schematic view. The supervision device 9 includes an optical gas detector 8 and a thermal flow detector 1.

The thermal flow detector 1 exemplarily includes an upstream thermoelectric element 10a as upstream temperature sensor, a downstream thermoelectric element 10b as downstream temperature sensor, and a middle thermoelectric element 10c that is arranged between the upstream thermoelectric element 10a and the downstream thermoelectric element 10b and serves as heating element. The flow detector 1 further includes a flow detector evaluation unit 3 that generates the flow detector signal from the electric raw signals that are provided by the thermoelectric elements, in particular the upstream thermoelectric element 10a and the downstream thermoelectric element 10b.

The optical gas detector 8 exemplarily includes two optical emitters and one optical receiver in an arrangement as explained further below in more detail, as well as a gas detector evaluation unit that generates the gas detector signal from the electric raw signal that is provided by the optical receiver.

The gas detector 8 and the flow detector 1 are operatively coupled to the processing unit 90 and provide the gas detector signal and the flow detector signal thereto. The processing unit 90 is realized by corresponding circuitry and/or software/firmware code that may be implemented in a microcontroller, microcomputer, or the like. The processing unit 90 is functionally coupled with the pump control unit 6 and/or general control circuitry of an ambulatory infusion pump and may further be fully or partly integral with the pump control unit and/or general control circuitry of an ambulatory infusion pump. Similarly, the gas detector evaluation unit and the flow detector evaluation unit 3 may be fully or partly integral with the processing unit 90, the pump control unit 6 or general control circuitry and may be realized by hardware, software/firmware, or a mixture thereof.

In operation, a drug container 5 is coupled with an infusion cannula 29 via a flow channel 20. The gas detector 8 is, in an operational configuration, coupled with the flow channel 20 at a gas detection location and the flow detector 1 is coupled with the flow channel 20 at a flow detection location downstream from the gas detection location. At its downstream side, in particular down-stream of the flow detector 1, the flow channel 20 runs into an infusion line 20b that, in turn, runs into the infusion cannula 29 at its downstream end. The flow channel 20 and the infusion line 20b may be realized, all or in part, by a common structure, or be structurally distinct. It is noted that both the gas detector 8 and the flow detector 1 do not directly interact with the liquid and/or gas inside the flow channel 20 and do not influence the flow, but couple indirectly via flow channel walls.

In an operational configuration, the drug container 5 is operatively coupled to a pump drive unit 4 for metered volumetric drug administration. The pump drive unit 4 is operatively coupled to and controlled by a pump control unit 6 that controls metered drug administration.

In an embodiment, the drug container 5 is a primary drug reservoir, e.g. in form of a cylindrical cartridge, with a typically filling volume in a range of e.g. 1 ml to 4 ml for the case of the drug being an insulin formulation. In this case, the overall device of the ambulatory infusion pump may be a syringe driver as well known in the art. Alternatively, the drug container 5 is a dosing cylinder of a downstream dosing unit as disclosed, e.g., in EP1970677A1 or EP2163273A1, that alternatively couples with a primary liquid drug reservoir (not shown), e.g. a cartridge or pouch, and the flow channel 20 via a switching valve and from which drug is metered respectively administered in a metered way in incremental drug pulses.

The arrangement of FIG. 1 is part of an ambulatory infusion system. In particular, the flow detector 1 and the gas detector 8 are typically integral part of an ambulatory infusion device that further includes components such as a pump control unit 6 and a pump drive unit 4. The fluidic distance L1 between the gas detection location and the flow detection location is typically in a range of 0.5 cm to 5 cm. The fluidic distance L2 from the flow detection location to the infusion cannula 29, i.e. the length of the infusion line 20b, may be in the same range in case of the ambulatory infusion device being carried as patch pump device that is directly attached to the skin. If the ambulatory infusion device is, e.g., carried via a belt clip or in a trousers' pocket, the fluidic distance L2 is in a typical range of 30 cm to 100 cm. The flow detector 1 is designed to detect the administration of a drug pulse, in particular to detect the temporary temperature distortion between the upstream thermoelectric element 10a and the downstream thermoelectric element 10b that results from the administration of a drug pulse. It can, however, in some embodiments not reliably distinguish between the presence of static (non-flowing) liquid on the one hand and non-flowing or flowing gas on the other hand at the flow detection location. In both cases, the flow detector signal may be a now-flow signal.

Since the fluidic path is unbranched from the liquid drug reservoir 5 to the infusion cannula 29 and is further substantially non-elastic, the fluidic flow is necessarily equal over the whole fluidic path and any amount of fluid (being it liquid, gas or a combination thereof) that is displaced out of the drug container 5 accordingly results in the same amount being administered via the infusion cannula 29 (assuming a substantially constant pressure as mentioned before). Also, any infinitesimal fluid amount that passes the gas detection location at a time to will pass the flow detection location at a later time t1, with the time delay t1-t0 being the time in which an expected delay volume that corresponds to the inner volume V1 of the flow channel (with length L1) between the gas detection location and the flow detection location is administered respectively displaced out of the drug container 5.

A corresponding relation holds true for the liquid-to-gas transition that forms the downstream front of a gas bubble and the gas-to liquid transition that forms the upstream front of a gas bubble. The volume that is administered between the downstream front and the upstream front of a gas bubble passing the gas detection location or the flow detection location corresponds to the bubble volume VB.

While both time delays and administered respectively displaced fluid volumes may equivalently be used for computational purposes, using displaced volumes is generally favourable because the displaced volume is well controlled by the volumetric metering pump as explained before, while timing may be more complex due to the typically non-continuous and pulsed administration.

In dependence of the specific design and the administration rate, the time delay that corresponds to the expected delay volume may be in a range of typically 15 minutes to an hour or more. It is noted that, while the distance L1 between the gas detection location and the flow detection location is design-given, the actual time delays as explained before are dependent on the administration rate and therefore generally vary as a function of time.

In the following, reference is additionally made to FIG. 2a, 2b, illustrating the operation of an exemplary gas detector 8. FIG. 2a shows the situation if the inner volume or lumen 22 of the flow channel 20 is filled with liquid drug in the area of the gas detector 8, in particular at the gas detection location. The first optical emitter 81 and the optical detector 80 are both arranged on one side of the flow channel 20, while the second optical emitter 82 is arranged on the opposite side of the flow channel 20. In the situation shown in FIG. 2a, the first optical beam 810 that is emitted by the first optical emitter 81 passes through the flow channel 20, including the channel wall 21 and the liquid drug in lumen 22. The first optical beam 810 exits the flow channel 22 at the side opposite to the first optical emitter 81 without hitting the optical detector 80. The second optical beam 820 that is emitted by the second optical emitter 82, in contrast, also passes through the flow channel 20, but hits the optical detector 80 unit due to its arrangement on the opposite side of the flow channel 20. The optical detector 80 is accordingly hit by the second optical beam 820, but not the first optical beam 810.

FIG. 2b illustrates the situation if a gas bubble B is present in lumen 22 at the gas detection location. Now, neither the first optical beam 810 nor the second optical beam 820 may pass through the flow channel 20, but are reflected totally at the border surface between channel wall 21 and the gas bubble due to the different refractive indices. The first optical beam 810 hits, after being reflected, the optical detector 80, while the second optical beam 820 does not hit the optical detector 80.

The first optical emitter 81 and the second optical emitter 82 are controlled by the gas detector evaluation unit 85 in a well-defined and time-variable manner. The gas detector evaluation 85 unit assesses the output signal of the optical detector 80 in relation to the actuation of the first and second optical emitter, 81, 82, thereby distinguishing whether the optical detector 80 is hit by the first optical beam 810 or the second optical beam 820. In a practical implementation, the first optical emitter 81 and the second optical emitter 82 are activated alternatively. In another practical implementation, they are each controlled with a time-varying e.g. sinusoidal control signal to emit an optical beam of accordingly varying intensity. The relation between the output signal of the optical detector 80 in relation to the actuation of the first and second optical emitter, 81, 82, may for example be done by the gas detector evaluation unit 85 via a lock-in circuit or cross correlation.

It is noted that in schematic FIGS. 2a, 2b, the first optical beam 810 and the second optical beam 820 hit the flow channel 20 at slightly different positions and accordingly have an offset with respect to each other along the flow direction F. In practical embodiments, however, the cross section of the flow channel 20 is sufficiently small to neglect this offset. The lateral dimension of the flow channel 20 should generally be small, for example in a range of 0.2 mm to 0.5 mm.

The walls 21 of the flow channel 20 are, at least in the area of the optical detector 8, optically transparent in the relevant wavelength range, thus allowing optical beam's 810, 822 to enter and exit. Furthermore, the walls 21 of the flow channel 20 are favorably planar respectively flat.

The relative arrangement of the optical detector 80, the first and second optical emitter 81, 82, and, in an operational configuration, the flow channel 20, is such that the first optical beam 810 and the second optical beam 820 intersect, in the case of FIG. 2a, in a point on the wall surface 21 pointing towards the optical detector 80 and the first optical emitter 81. This is also the point where the first optical beam 810 hits the channel wall 21 and is reflected in case of FIG. 2b.

Figure 3:
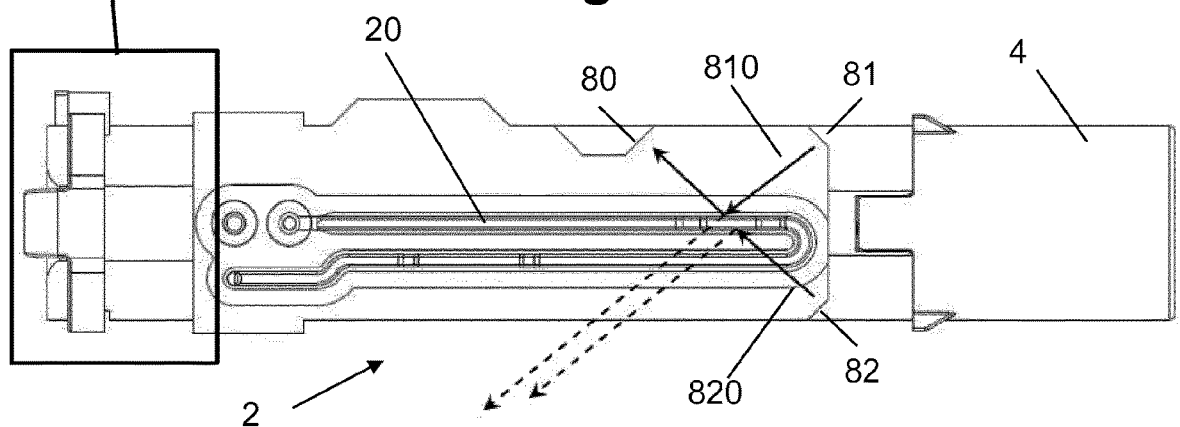
FIG. 3 schematically shows the integration of a gas detector according FIG. 2 in a fluidic device.
Figure 2:
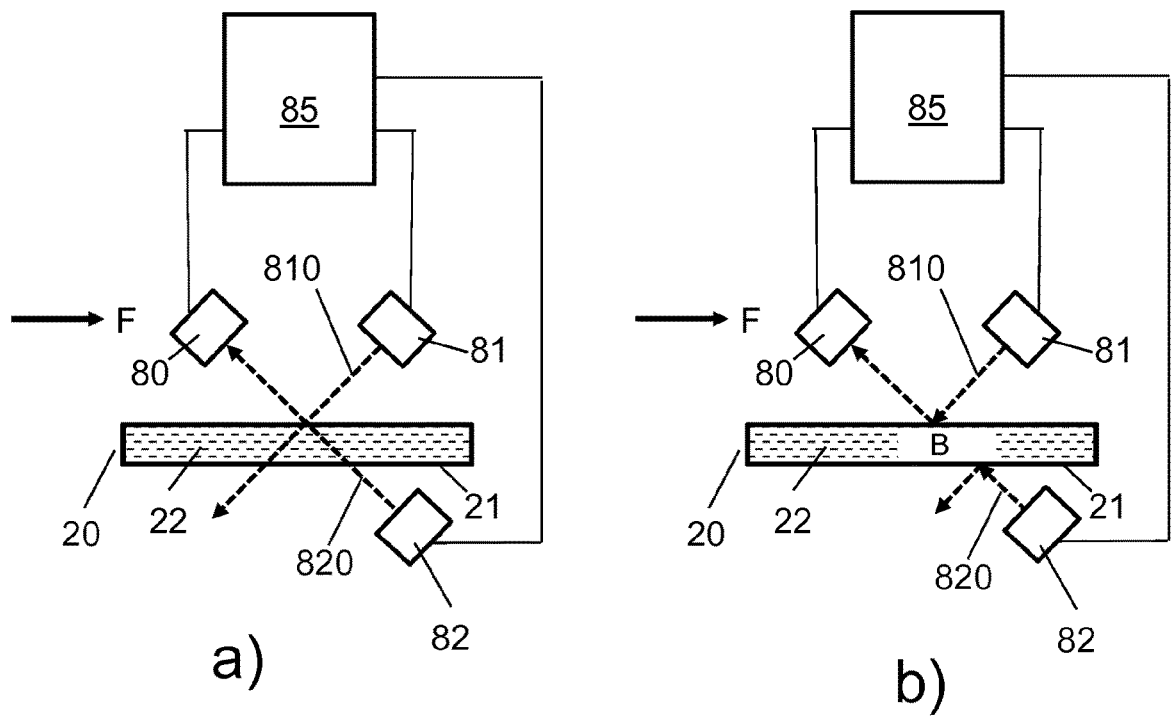
FIG. 2 schematically shows the operation of an exemplary gas detector.

In the following, reference is additionally made to FIG. 3. FIG. 3 illustrates the cooperation of a gas detector 8 according to FIG. 1, FIG. 2, and a fluidic device 2 that includes the flow channel 20. The fluidic device 2 exemplarily is a dosing unit in general accordance with the disclosure of EP1970677A1. The fluidic device 2 includes a dosing cylinder (not visible in FIG. 3). Inside the dosing cylinder, a plunger is received in sliding and sealing engagement, thus forming a syringe-like configuration. The plunger is, in operation, realisably operatively coupled to a motoric pump drive unit 4 with a spindle drive for controlled displacement of the plunger in incremental steps. The fluidic device 2 further includes a valve unit 28 in fluidic coupling with the inner volume of the dosing cylinder. Via a valve drive unit or valve actuator (not shown), the valve unit 28 is controlled to fluidic couple the inner volume of the dosing cylinder alternatively with a primary drug reservoir (not shown) or the flow channel 20, with an outlet of the flow channel 20 coupling to the infusion line 20b. The fluidic device 2 has an infusion device coupler as mating coupling structure for releasable coupling with an ambulatory infusion device such that the optical detector 80 and the first and second optical emitter, 81, 82 optically interact with the flow channel 20 and the flow detector 1 interacts and in particular thermally couples to the flow channel 20 in accordance with the principle as illustrated in FIG. 2a, 2b.

Figure 4:
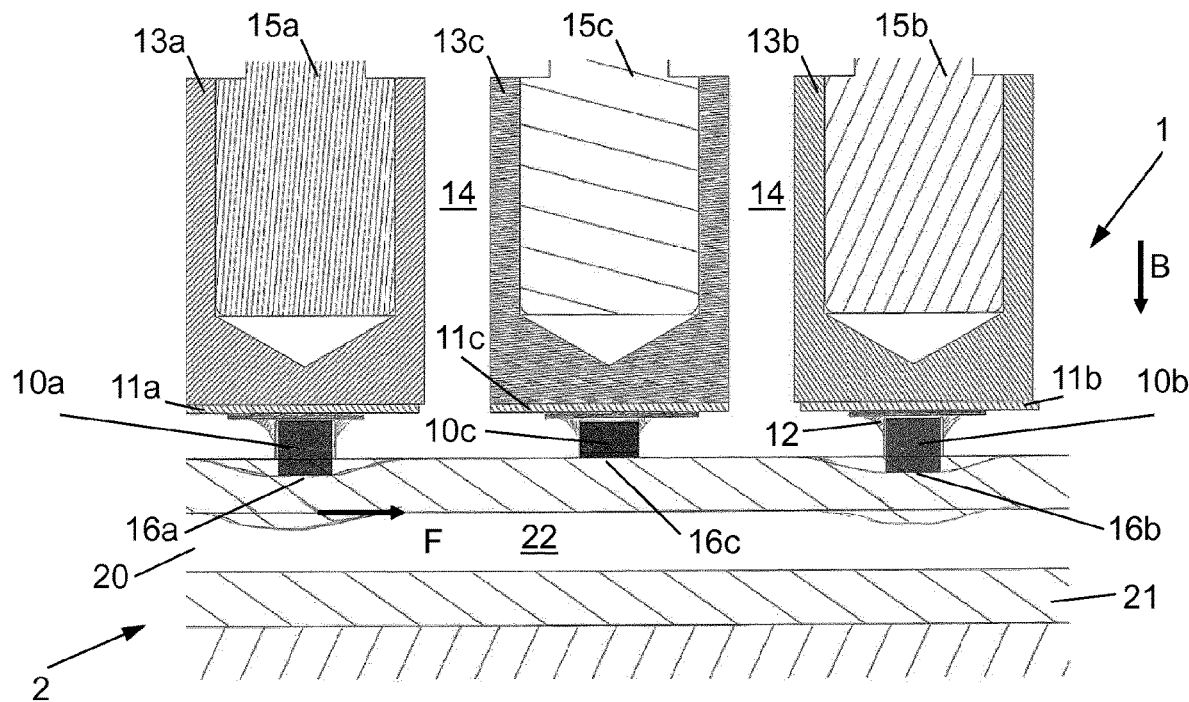
FIG. 4 shows an embodiment of a flow detector in operative coupling with a flow channel in a schematic side view.

In the following, reference is first made to FIG. 4, showing an exemplary embodiment of a flow detector 1 and a fluidic device 2 in a schematic structural view. The flow detector 1 may be part of a supervision device in accordance with the present disclosure.

The flow detector 1 includes an upstream thermoelectric element 10a, a downstream thermoelectric element 10b, and an optional middle thermoelectric element 10c. In this example, the upstream thermoelectric element 10a and the downstream thermoelectric element 10b are NTC thermistors of identical characteristics, while the middle thermoelectric element 10c is a heating element (resistor). In an embodiment without the middle thermoelectric element 10c, the upstream thermoelectric element 110a and the downstream thermoelectric element 10b are NTC thermistors of favorably different characteristics, in particular different resistance.

The thermoelectric elements 10a, 10b, 10c are surface-mounted elements or surface-mounted devices (SMDs), each of them being mounted on a corresponding separate element carrier 11a, 11b, 11c in form of flexible circuit board elements. The thermoelectric elements 10a, 10b, 10c are mounted on and connected to the corresponding printed circuit board elements 11a, 11b, 11c via soldering joints 12 (typically two soldering joints 12 for each of the thermoelectric elements 10a, 10b, 10c).

On the opposite side of the printed circuit board elements 11a, 11b, 11c, corresponding insulator elements 13a, 13b, 13c are arranged. Each of the insulator elements 103a, 13b, 13c has a central blind bore in which an end section of a corresponding biasing element 15a, 15b, 15c is arranged. The biasing element 15a is the upstream biasing element, the biasing element 15c the down-stream spring element and the biasing element 15c the middle biasing element of the flow detector 1. The opposite end of the biasing elements 15a, 15b, 15c are supported by a support structure (not shown) that may be part of an ambulatory infusion device housing. The biasing elements 15a, 15b, 15c are exemplarily realized as coil springs. The biasing elements 15a, 15b, 15c each separately exert a biasing force onto the corresponding carrier element 11a, 11b 11c and the thermoelectric elements 10a, 10b, 10c in direction B.

The upstream element carrier 11a and the middle element carrier 11c, as well as the middle element carrier 11c and the downstream element carrier 15b are pairwise separated by a gap 14 of identical width.

The fluidic device 2 includes the flow channel 20 with a hollow lumen 22 of circular cross section that is circumferentially surrounded by a flow channel wall 21, in combination forming a tubular structure. Other types of flow channels may be used as well.

At a side adjacent to the flow detector 1 respectively the thermoelectric elements 10a, 10b, 10c, the fluidic device 2 includes a plate-shaped abutment element 23 that supports the flow channel and absorbs the contact forces respectively biasing forces. The flow channel exemplarily extends along a straight line with the flow direction being indicated by F.

The upstream thermoelectric element 10a contacts the flow channel 20 at an upstream position 16a where the elastic flow channel wall 21 is accordingly slightly deformed under the influence of the contact force respectively biasing force. The same holds true for the downstream thermoelectric element 10b that contacts the flow channel 20 at a downstream position 16b and the middle thermoelectric element that contacts the flow channel 20 at the middle position 16c. The area of the upstream contact position 16a, the downstream contact position 16b, and the middle contact position 16c, in combination, forms the flow detector coupling area.

Figure 5:
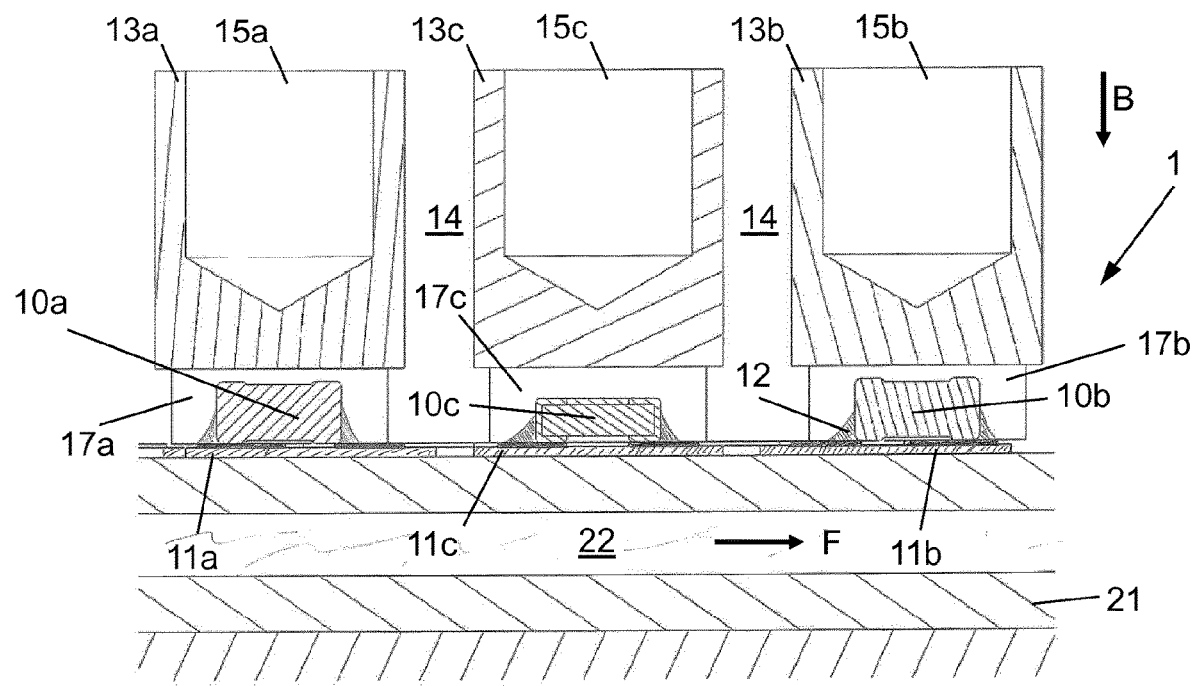
FIG. 5 shows a further embodiment of a flow detector in operative coupling with a flow channel in a schematic side view.

In the following, reference is additionally made to FIG. 5, showing a further exemplary embodiment of the flow detector 1 together with components of a fluidic device 2. In a number of aspects, the embodiment of FIG. 5 is identical to the before-discussed embodiment of FIG. 4. The following discussion is focused on the differences.

In the embodiment of FIG. 4, the thermoelectric elements 10a, 10b, 10c are arranged on the side of the carrier elements (flexible printed circuit board elements 11a, 11b, 11c) that face the flow channel 20 and the flow detector coupling area. The thermoelectric elements 10a, 10b, 10c accordingly directly contact the flow channel 20 respectively the flow channel wall 21. In the embodiment of FIG. 5, in contrast, the thermoelectric elements 10a, 10b 10c are arranged on the corresponding carrier elements 11a, 11b, 11c on a side pointing away from the flow channel 20 and the channel contact area, but pointing towards the biasing elements 15a, 15b, 15c instead.

The thermoelectric elements 10a, 10b, 10c accordingly contact the flow channel 20 indirectly via the carrier elements 11a, 11b, 11c rather than directly. The result is a further improvement of the thermal coupling, as explained before in the general description. Additionally, it can be seen that the contact area between the carrier elements 11a, 11b, 11c and the flow channel 20 is larger as compared to the thermoelectric elements 10a, 10b, 10c. The deformation of the flow channel wall 21 is accordingly favourably reduced or even avoided.

In order to improve the desired terminal isolation between the thermoelectric elements and the (typically metallic) biasing elements, an optional insulator cap 17a, 17b, 17c is provided in this embodiment for each of the thermoelectric element and the corresponding insulator 13a, 13b, 13c and biasing element 17a, 17b, 17c, thus preventing a direct contact between the thermoelectric elements 10a, 10b, 10c and the insulators 13a, 13b, 13c with the biasing elements 15a, 15b, 15c. The insulator caps 17a, 17b, 17c are made from a material of low thermal conductivity, typically plastics, and put over the thermoelectric elements 10a, 10b, 10c. The insulator caps 17a, 17b, 17c may, e.g. be glued onto the carrier elements 11a, 11b, 11c after soldering of the thermoelectric elements 10a, 10b, 10c. The insulator caps may in principle also be realized integral with the insulators 13a, 13b, 13c.

Figure 6:
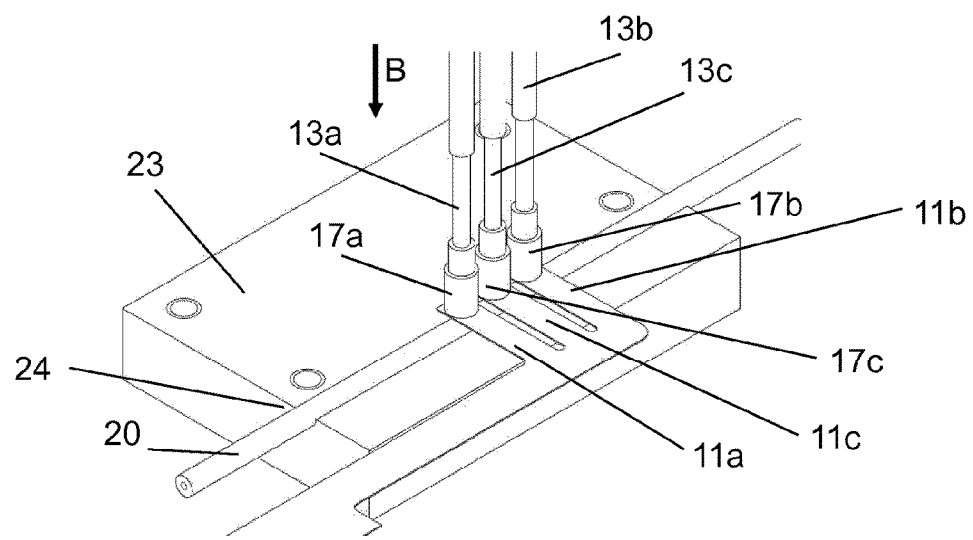
FIG. 6 shows the flow detector of FIG. 5 in a schematic three-dimensional view.

In the following, reference is additionally made to FIG. 6, showing the arrangement form FIG. 5 in a perspective view.

It can be seen that the carrier elements (flexible printed circuit board elements) 11a, 11b, 11c are finger-shaped and extend parallel from a common flexible printed circuit board 11d, traverse to the extension direction of the flow channel 20. It can further be seen that flow channel 20 is partly arranged in a groove 24 of the abutment element 23, the groove 24 positioning the flow channel 20 relative to the flow detector 1. A corresponding arrangement may also be used in the embodiment of FIG. 4.

FIG. 4 to FIG. 6 show embodiments with three separate thermoelectric elements, with the middle thermoelectric element 10c being distinct from the upstream and downstream thermoelectric elements 10a, 10b as temperature sensors. Embodiments where the upstream thermoelectric element 10a serves as both heating element and as upstream temperature sensor may be realized in the same way, omitting, however, the middle thermoelectric element 10c and associated components.

Figure 7:
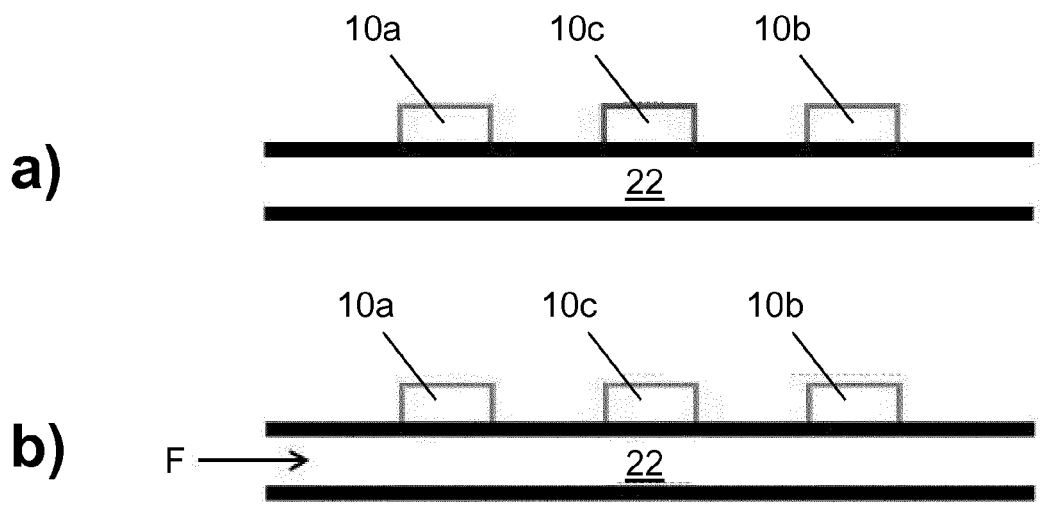
FIG. 7 illustrates the operation of an embodiment of a flow detector.

In the following, reference is additionally made to FIG. 7a, 7b, illustrating the operation of an embodiment of a flow detector with three thermoelectric elements. FIG. 7a shows the situation shortly before a drug pulse is administered. Both the upstream thermoelectric element 10a as upstream temperature sensor and the downstream thermoelectric element 10b as downstream temperature sensor are at a low base temperature that corresponds to a temperature that can be measured in a static state without liquid flow in the lumen 22. The middle thermoelectric element 10c as heating element heats the liquid in its proximity to an increased temperature. Without liquid flow, the heat would be transported equally into the upstream direction (against the flow direction F) and the downstream direction (with the flow direction F) via thermal conduction, resulting in substantially equal temperatures at the upstream thermoelectric element 10a and the downstream thermoelectric element 10b.

FIG. 7b illustrates the situation shortly after switching off the heating via middle thermoelectric element 10c and administering a drug pulse. Now, the heat is transported with the drug in the lumen 22 in the flow direction F, resulting in the downstream thermoelectric element 10b as downstream temperature sensor being at a higher temperature than the upstream thermoelectric element 10a as upstream temperature sensor. The measured temperature difference between the downstream thermoelectric element 10b and the upstream thermoelectric element 10a is evaluated in order to determining whether or not a liquid flow has actually occurred. Optionally, the heating may be continued during the measurement.

Figure 8:
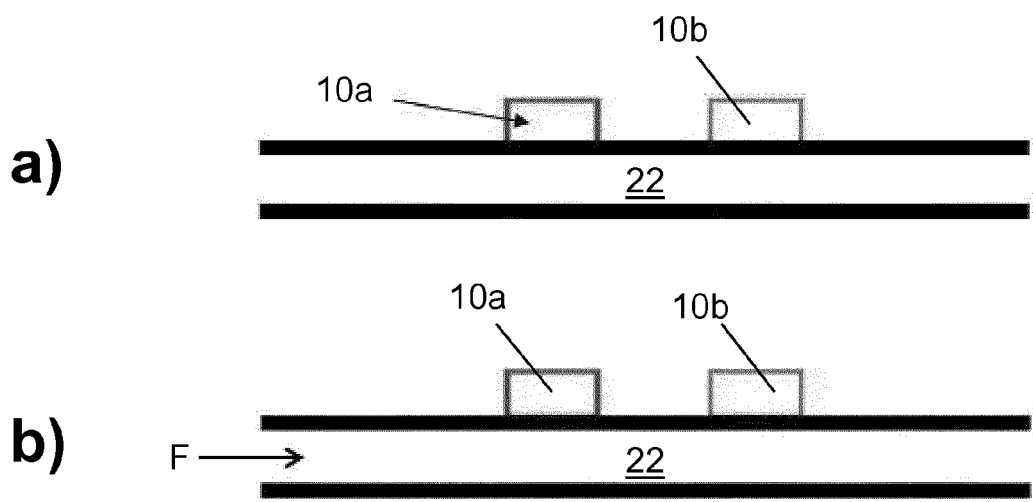
FIG. 8 illustrates the operation of a further embodiment of a flow detector.

FIG. 8a, 8b show situations corresponding to FIG. 7a, 7b for an embodiment with only two thermoelectric elements, where the upstream thermoelectric element 10a serves as both heating element and upstream temperature sensor and the downstream thermoelectric element 10b serves as downstream temperature sensor. In FIG. 7a, the upstream thermoelectric element 10a is operated as heating element that heats the liquid in its proximity to an increased temperature, while the downstream thermoelectric element 10b is at a lower temperature. As discussed further below in the context of FIG. 9 in more detail, the upstream thermoelectric element 10a heats the liquid continuously or substantially continuously, resulting in the upstream thermoelectric element 10a being at a higher temperature than the downstream thermoelectric element 10b. Since, however, heated liquid drug is, in FIG. 8b, transported towards the downstream thermoelectric element 10b and replaced by colder liquid from upstream of the flow detector, the temperature at the upstream thermoelectric element 10a will be somewhat decreased and the temperature at the downstream thermoelectric element 10b will be somewhat increased. The temperature difference between the upstream thermoelectric element 10a and the downstream thermoelectric element 10b is accordingly reduced because of the liquid drug flow.

Figure 9:
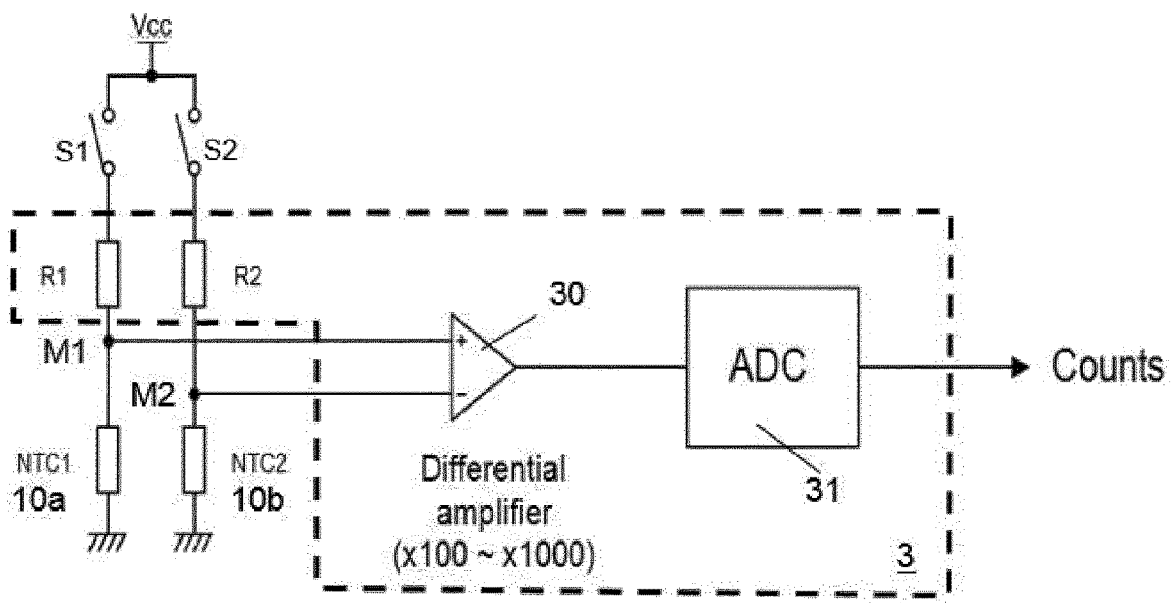
FIG. 9 shows an embodiment of the coupling of a flow detector with a flow detector evaluation unit.

In the following, reference is additionally made to FIG. 9, illustrating an embodiment of a flow detector evaluation unit 3 in interaction with the thermoelectric elements 10a, 10b. In this embodiment, the upstream thermoelectric element 10a and the downstream thermoelectric element 10b are NTCs (also referred to as NTC1 and NTC2) of exemplary identical characteristics and are arranged in series with corresponding fixed resistors R1 and R2 such that fixed resistor R1 and NCT1 respectively fixed resistor R2 and NTC2 each form a a branch of a Wheatstone bridge that is selectively connectable to a voltage supply Vcc via switches S1 S2 that are closed for operation and otherwise open for energy efficiency reasons. The differential voltage between the midpoints M1, M2 of the two branches is fed to a differential amplifier 30 that is typically realized based on an operational amplifier (op-amp). The output of the differential amplifier 30 is fed into an analogue-to-digital converter (ADC) 31, the output of which (referenced as "counts" is) is accordingly dependent on favourably substantially proportional to the temperature difference between NTC1 and NTC2.

The upstream thermoelectric element 10a (NTC1) may serve as both heating element and upstream temperature sensor with switch S1 being closed. After a heating period, switch S2 is additionally closed and the downstream thermoelectric element 10b (NTC2) is additionally powered for measuring the temperature difference. During the preceding heating time, switch S2 is opened in order to prevent NTC2 from heating the liquid at the downstream position. If no flow detection is carried out, both S1 and S2 are favourably open in order to save energy and avoid an unnecessary and generally unfavourable liquid heating.

In particular in embodiments of the above-described type where the first thermoelectric element 10a and the second thermoelectric element 10b are of identical characteristics and the upstream thermoelectric element 10a additionally serves as heating element, the downstream thermoelectric element 10b is only powered for a short period of time (typically in the range of some milliseconds) for the temperature measurement and is in particular not powered during the preceding heating time, as it would otherwise heat the liquid in the same way as the upstream thermoelectric element.

In a variant (not shown), a branch with a further switch and a further resistor in serial arrangement (like resistor R1 and switch S1) is provided in parallel to resistor R1 and switch S1, such that NTC1 may be powered alternatively via the further switch and the further resistor. The further resistor is favourably considerably smaller as compared to the resistor S1 and NTC1 is powered for the heating time via the further switch and further resistor, resulting in a favourable shortened heating time. The heating may be controlled by operating the further switch via pulse-width modulation. For the subsequent temperature difference measurement, the further switch is opened and switches S1, S2 are closed as explained before.

In a further variant, both the upstream thermoelectric element 10a (NTC1) and the downstream thermoelectric element 10b (NTC2) serve as temperature sensors only and an additional middle thermoelectric element is provided as dedicated heating element.

Figure 10:
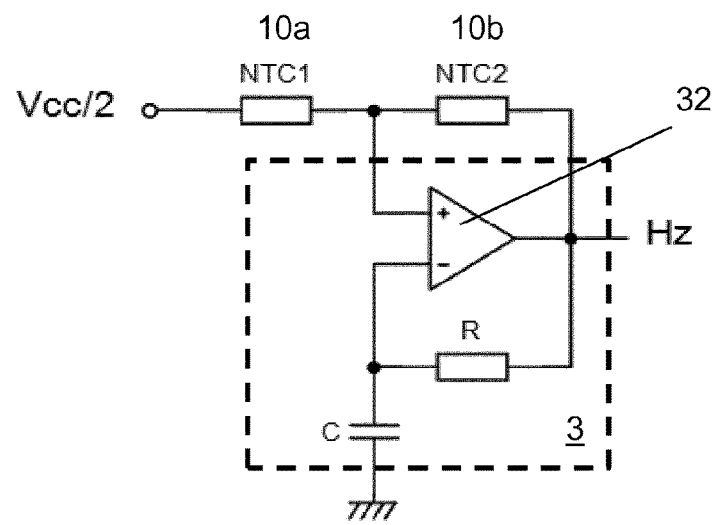
FIG. 10 shows the coupling of a flow detector with a flow detector evaluation unit according to a further embodiment.

In the following, reference is additionally made to FIG. 10, illustrating a further embodiment of a flow detector evaluation unit 3 in interaction with the thermoelectric elements 10a, 10b. This type of embodiment is particularly favourable if the upstream thermoelectric element 10a serves as both upstream temperature sensor and as heating element, and the upstream thermoelectric element 10a and the downstream thermoelectric element 10b are NTCs of different characteristics, in particular different resistance. The resistance of the upstream thermoelectric element 10a is considerably lower than the resistance of the downstream thermoelectric element 10b in order to prevent the downstream thermoelectric element 10b from heating the liquid in the same way as the upstream thermoelectric element 10a. Favorably, the resistance ration may be about 1:10 or more.

In the embodiment of FIG. 10, an e.g. op-amp-based comparator 32 forms, together with the thermoelectric elements NTC1, NTC2, a Schmitt-Trigger, the two thresholds of which are determined by the resistances of NTC1 respectively NTC2. Further, an oscillator of given frequency is present and coupled to the comparator 32. The oscillator is exemplarily realized as simple R-C oscillator with a frequency of, e.g. some Kilohertz (kHz) to some Megahertz (MHz). As a result, the output of the comparator 32 provides a square signal, the frequency of which depends on the temperature difference between NTC1 and NTCs and can be measured in a straight forward way.

Modern microcontrollers typically include components such as comparators, reference voltage supplies, timers and highly accurate crystal oscillators. Based on such a microcontroller, an evaluation unit 3 according to FIG. 10 may be realized with a very small number of further components (the resistor R, the capacitor C, and the NTCs as thermoelectric elements), thus providing a very compact and cost-efficient solution.

The flow detector evaluation unit 3, e.g. according to FIG. 9 or FIG. 10, may be realized partly or fully integral further functional units or circuitry, e.g. a pump control unit of an ambulatory infusion device.

Figure 11:
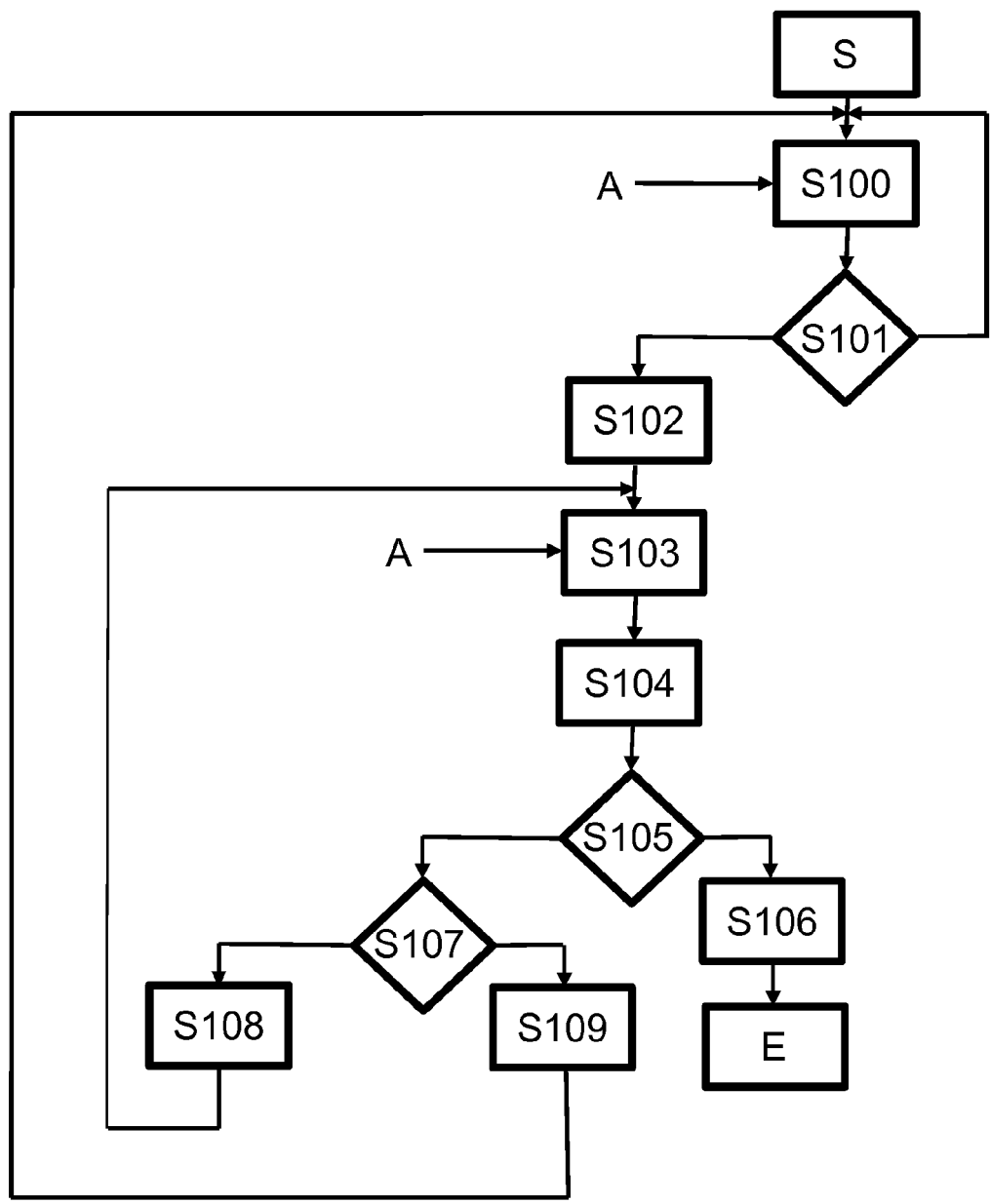
FIG. 11 illustrates an exemplary operational flow for the operation of a gas detector.
Figure 12A:
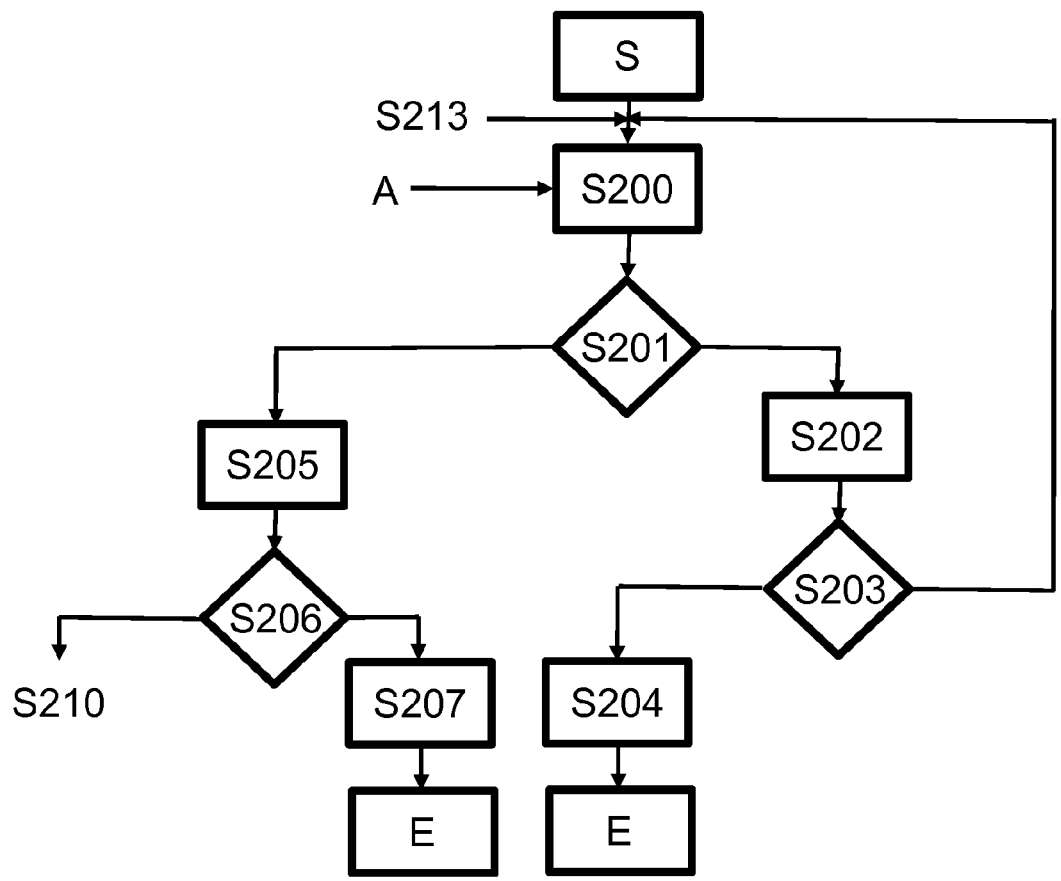
FIG. 12a, 12b illustrate an exemplary operational flow for the operation of a flow detector.
Figure 12B:
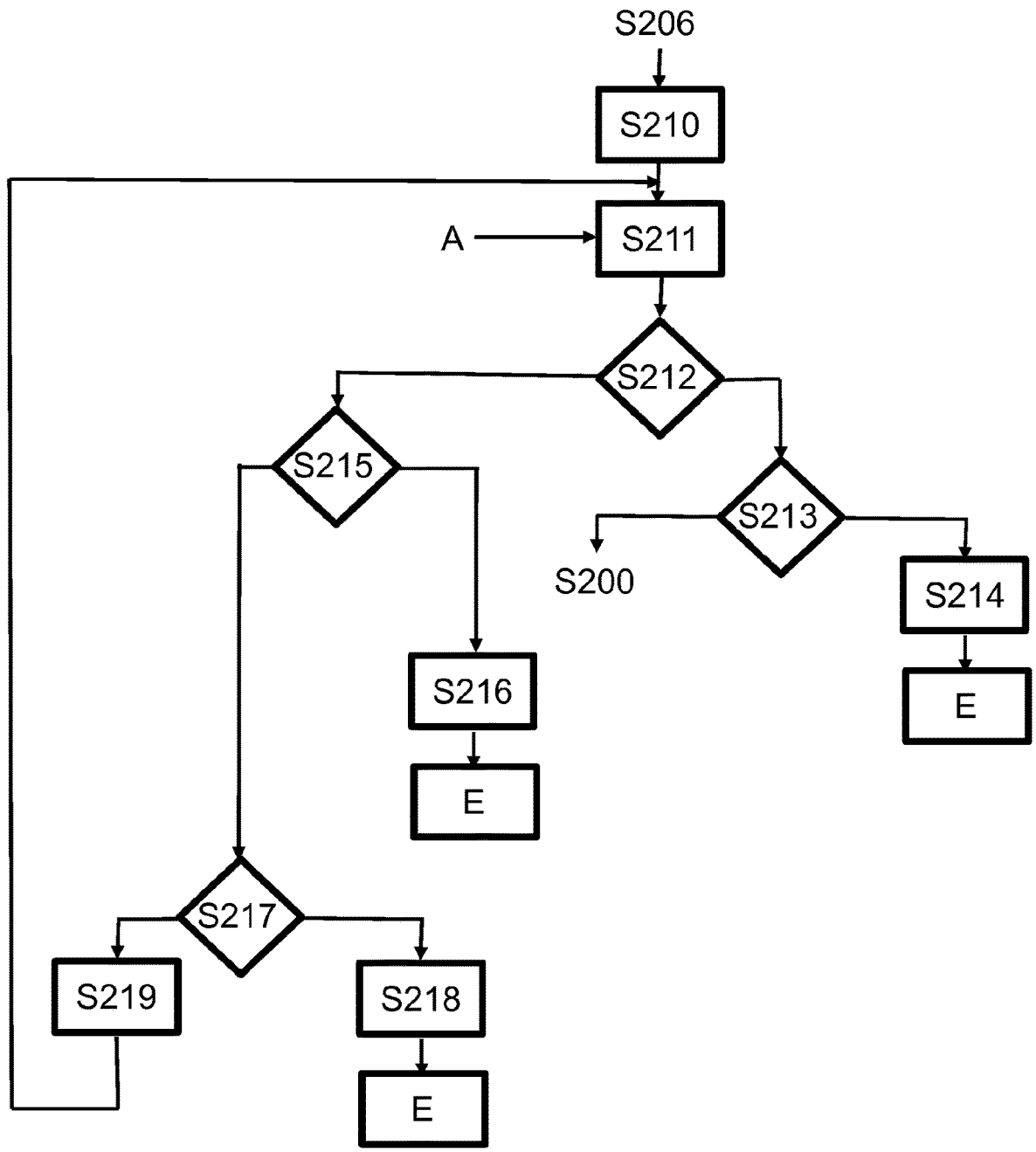

In the following, reference is additionally made to FIG. 11 and FIG. 12a, 12b, illustrating an exemplary method for supervising liquid drug administration and in particular operation of an embodiment of supervision device 9 in schematic flow charts. FIG. 11 is focused on the operation of the gas detector 8 and the evaluation of the gas detector signal, while FIG. 12 is focused on the operation of the flow detector 1 and the evaluation of the flow detector signal. In the following, it is assumed that the ambulatory infusion device is in a steady-state and that liquid drug is present in the flow channel 20 at the beginning.

First, reference is made to FIG. 11. In step S100 the evaluation unit 90 receives information from the pump control unit 6 that a drug pulse is administered (indicated by arrow "A") and determines the gas detector signal. In subsequent step S101, the operational flow branches in dependence of the gas detector signal. If the gas detector signal indicates that liquid is present in the flow channel at the gas detection location, the operational flow continues with step S100 and no action is carried out until the next drug pulse is administered.

If, in contrast, the flow detector signal indicates that gas is present in the flow channel 20 at the gas detection location, the downstream front of a gas bubble has passed the flow detection location and step S102 is carried out. In step S102, a bubble volume counter is initialized with the volume of the administered drug pulse (step S100).

In subsequent step S103, the evaluation unit 90 receives, like in step S100, information that the next drug pulse is administered and determines the gas detector signal.

In subsequent step S104, it is determined whether the volume that has been administered respectively displaced since the downstream front of the gas bubble passing the gas detection location corresponds to the expected delay volume. This information is used for evaluating the flow detector signal as explained further below with reference to FIG. 12.

In subsequent step S105, the bubble volume counter is compared with an alarming threshold volume and the operational flow branches in dependence of the comparison result. If the bubble volume according to the bubble volume counter exceeds the alarming threshold volume, an alarm signal is generated in step S106 and the operation ends. It is noted that steps S105 and S106 are optional and may be omitted in a variant.

Otherwise, the operational flow proceeds with step S107 where it branches in dependence of the gas detector signal as determined in step S103.

If the gas detector signal in step S103 indicates that gas is present at the gas detection location, the operational flow proceeds with step S108 where the bubble volume counter is increased by the pulse volume of the administration in step S103 and the operational flow proceeds with step S103.

If the gas detector signal in step S104 indicates that liquid is present at the gas detection location, the upstream front of the gas bubble has passed the gas detection location and the operational flow proceeds with step S109. In step S109 it is registered that the complete gas bubble has passed the gas detection location and the operational flow subsequently proceeds with step S100. If a next following gas bubble passes the gas detection location, the bubble counter volume as mentioned before is not further increased, but a further bubble volume counter is initialized.

In the following, reference is additionally made to FIG. 12a. In step S200, the evaluation unit 90 receives information from the pump control unit 6 that a drug pulse is administered (indicated by arrow "A"). Consequently, the flow detector 1 is operated during the administration and the flow detector signal is determined.

In subsequent step S201, the operational flow branches in dependence of the flow detector signal. If the flow detector signal indicates a liquid drug flow, the operational flow proceeds with step S202 where it is determined whether the expected delay volume has been administered respectively displaced since the downstream front of a gas bubble has passed the gas detection location (S102 in FIG. 11) and the operational flow branches in dependence of the result in step S203. If the expected delay volume has not been administered respectively displaced since the downstream front of a gas bubble having passed the gas detection location, the detection of a liquid drug flow in step S200 is indicative of a the correct administration of a drug pulse. Consequently, the operational flow proceeds with step S200 and the administration of the next pulse is awaited. If, on the other hand, the expected delay volume has been administered, the flow detector 1 should have produced a no-flow signal in step S200 and the presence of a liquid drug flow indicates the presence of an error condition. Consequently, an alarm signal is generated in step S204 and the operational flow ends.

If the flow detector signal is a no-flow signal in step S201, the operational flow proceeds with step S205. In step S205 it is determined (like in step S202 as explained before) whether the expected delay volume has been administered respectively displaced since the downstream front of a gas bubble has passed the gas detection location. If this is not the case, the no-flow signal is indicative of an occlusion downstream of the flow detection location. Consequently, an alarm signal is generated in step S207 and the operational flow ends.

If the result is affirmative in step S205, the no-flow signal in step S200 is indicative for a gas bubble passing the flow detector 1. Passing of the gas bubble is expected based on the gas detector signal. The operational flow proceeds with the steps as shown in FIG. 12b to which additional reference is made in the following.

In step S210, a secondary bubble volume counter is initialized with the volume of the administered drug pulse (step S200). The secondary bubble volume counter operates in substantially the same way as the before-explained bubble volume counter, but is based on the flow detector signal rather than the bubble detector signal.

In subsequent step S211, the evaluation unit 90 receives, like in step S200, information that the next drug pulse is administered. Consequently, the flow detector 1 is operated during the administration and the flow detector signal is determined.

In subsequent step S212, the bubble volume counter is compared with the secondary bubble volume counter an alarming threshold volume and the operational flow branches in dependence of the comparison result.

If the content of both the bubble volume counter and the secondary bubble volume counter match, it is expected that a gas bubble has passed the flow detection location. In this case, the operational flow proceeds with step S213 where the operational flow branches in dependence of the flow detector signal as determined in step S211. If the flow detector signal in Step S211 indicated a liquid flow, it is confirmed that that gas bubble has passed the flow detection location and the operational flow proceeds with S200. If, in contrast the flow detector signal in step S211 is a no-flow signal even though the gas bubble should have passed the flow detection location, an alarm signal is generated in step S214 and the operational flow ends.

If it is determined in step S212 that the contents of the bubble volume counter and the secondary bubble volume counter do not match, the operational flow proceeds with step S215 where the operational flow further branches in dependence of the flow detector signal as determined in step S211.

The contents of the bubble volume counter and the secondary bubble volume counter not matching is, under correct operational conditions, indicative of a gas bubble presently passing the flow detection location. The flow detector signal as determined in step S211 is accordingly expected to be a no-flow signal. The flow detector signal nevertheless being indicative of a drug flow even though a gas bubble is expected to be passing the flow detection location, is indicative of an error condition. An alarm signal is accordingly generated in step S216 and the operational flow ends.

If the flow detector signal as determined in step S211 is a no-flow signal, the operational flow proceeds with step S217 where it is determined whether the content of the secondary bubble volume counter exceeds the content of the bubble volume counter. In the affirmative case, the operational flow proceeds with step S218 where an alarm signal is generated and the operational flow ends. This situation occurs, e.g., if an occlusion downstream of the flow detection location occurs while a gas bubble being present at the flow detection location.

Otherwise, the operational flow proceeds with step S219. This is the case if a gas bubble passes the flow detection location under correct operational conditions. In step S219, the secondary bubble volume counter is increased by the pulse volume of the administration in step S211 and the operational flow proceeds with step S211.

In a practical implementation, the operation as explained in context of FIG. 11, 12a, 12b may be modified in a number of way. For example, the operational flow as explained is based on the assumption that, under correct operational conditions, the expected delay volume is exactly met. In reality, however, both the flow detector signal and the gas detector signal are subject to tolerances and measurement uncertainty which may be considered when comparing the contents of the bubble volume counter and the further bubble volume counter. Furthermore, an alarm signal indicative of an occlusion may be generated if a now-flow signal is present for a number of consecutive pulses. A no-flow signal for a single or a small number of, e.g., 2 to 5 consecutive pulses may also result from a temporarily sticking piston and not necessarily from an occlusion.

The invention claimed is:

1. A supervision device for supervising liquid drug flow in a flow channel, the supervision device including:
   a flow detector operatively coupled with the flow channel and generating a flow detector signal indicating that a flow has been detected or the flow has not been detected in the flow channel at a flow detection location at a flow detection time;
   a gas detector operatively coupled with the flow channel and generating a gas detector signal indicating whether a liquid drug or a gas is present in the flow channel at a gas detection location at a gas detection time,
      the gas detection location being located a distance upstream from the flow detection location, and
      the flow detection time occurring an expected delay volume after the gas detection time; and
   a processing unit in operative coupling with the flow detector and the gas detector, wherein the processing unit is configured to determine, based on the gas detector signal and the flow detector signal, whether non-flowing liquid drug or a gas bubble is present at the flow detection location at the flow detection time,
   the processing unit being configured to determine that the gas bubble is present at the flow detector location at the flow detection time if the flow detector signal does not indicate a liquid drug flow at the flow detection time and the gas detector signal indicated the gas bubble at the gas detection location at the gas detection time.

2. The supervision device according to claim 1, configured to generate an alarm signal if non-flowing liquid drug is present at the flow detection location.

3. The supervision device according to claim 1, configured to determine a first gas bubble volume based on the gas detector signal, and to determine whether the flow detector signal matches the first gas bubble volume.

4. The supervision device according to claim 1, wherein the gas detector includes a first optical emitter, a second optical emitter, and an optical detector.

5. The supervision device according to claim 4, wherein the first optical emitter and the second optical emitter are arranged such that the flow channel extends between them.

6. The supervision device according to claim 4, wherein the first optical emitter, the second optical emitter and the optical detector are arranged such that
   a first optical beam that is emitted by the first optical emitter passes through the flow channel without hitting the optical detector and that a second optical beam that is emitted by the second optical emitter passes through the flow channel and hits the optical detector if liquid drug is present inside the flow channel at the gas detection location, and that the first optical beam is reflected and hits the optical detector and that the second optical beam is reflected without hitting the optical detector if gas is present inside the flow channel at the gas detection location.

7. The supervision device according to claim 4, wherein the supervision device is configured to control the first optical emitter to vary a first optical beam and to control the second optical emitter to vary a second optical beam with a defined timing relation, and wherein the processing unit is configured to determine, based on the timing relation, whether an optical beam that hits the optical detector is the first optical beam or the second optical beam.

8. The supervision device according to claim 1, wherein the flow detector is configured for releasable coupling with the flow channel in a channel coupling area and includes
   an upstream thermoelectric element and a downstream thermoelectric element, wherein the upstream thermoelectric element and the downstream thermoelectric element are arranged spaced apart from each other and movable independent from each other; and
   an upstream biasing element and a downstream biasing element, wherein the upstream biasing element acts on the upstream thermoelectric element, thereby biasing the upstream thermoelectric element towards the channel coupling area, and the downstream biasing element acts on the downstream thermoelectric element, thereby biasing the downstream thermoelectric element towards the channel coupling area independently from the upstream biasing element.

9. The supervision device according to claim 8, wherein the upstream thermoelectric element is carried by an upstream element carrier and the downstream thermoelectric element is arranged on a downstream element carrier, and a gap is present between the upstream element carrier and the downstream element carrier.

10. The supervision device according to claim 8, wherein the upstream thermoelectric element is arranged on an upstream flexible printed circuit board element and the downstream thermoelectric element is arranged on a downstream flexible printed circuit board element, wherein the upstream thermoelectric element is arranged on a side of the upstream flexible printed circuit board element pointing away from the channel coupling area and the downstream thermoelectric element is arranged on a side of the downstream flexible printed circuit board element pointing away from the channel coupling area.

11. An ambulatory infusion device, including:
   a pump drive unit, configured to administer liquid drug out of a drug container to a patient's body via a flow channel;
   a pump control unit, configured to control operation of the pump drive unit for continuous drug administration according to a time-variable basal infusion administration rate; and
   the supervision device according to claim 1 in operative coupling with the pump control unit.

12. The ambulatory infusion device according to claim 11, wherein the ambulatory infusion device is configured to determine when the gas bubble reaches an infusion site and to control the pump drive unit to administer a compensation volume, the compensation volume corresponding to a volume of the gas bubble, upon the gas bubble reaching an infusion site.

13. A method for supervising liquid drug administration via a flow channel, the method including:
   generating a flow detector signal using a flow detector in dependence of a flow in the flow channel at a flow detection location;
   generating a gas detector signal using a gas detector in dependence of whether liquid drug or gas is present in the flow channel at a gas detection location at a distance upstream from the flow detection location; and
   determining, based on the gas detector signal and the flow detector signal, that a gas bubble is passing the flow detection location using a processor if the flow detector signal does not indicate a liquid drug flow and an expected delay volume has passed after the gas detector signal detected the passing of the gas bubble.

14. The method according to claim 13, the method including generating an alarm signal if the flow detector signal not indicating the liquid drug flow is indicative of a situation of no drug flow.

15. A method for supervising liquid drug administration via a flow channel, the method including:
   generating a gas detector signal using a gas detector in dependence of whether liquid drug or gas is present in the flow channel at a gas detection location at a distance upstream from a flow detection location;
   generating a flow detector signal using a flow detector in dependence of a flow in the flow channel at the flow detection location after a flow of an expected delay volume; and
   determining that:
      a gas bubble is passing the flow detection location if the flow detector signal does not indicate a liquid drug flow and the expected delay volume has passed after the gas detector signal detected the passing of the gas bubble.

* * * * *